US007091026B2

(12) United States Patent
Franklin

(10) Patent No.: US 7,091,026 B2
(45) Date of Patent: Aug. 15, 2006

(54) ARTIFICIAL ENDONUCLEASE

(75) Inventor: Sonya Franklin, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 52 days.

(21) Appl. No.: 09/785,546

(22) Filed: Feb. 16, 2001

(65) Prior Publication Data

US 2002/0146788 A1  Oct. 10, 2002

(51) Int. Cl.
*C12N 9/22* (2006.01)
*C12N 15/55* (2006.01)
*C12P 19/34* (2006.01)
*C12Q 1/68* (2006.01)

(52) U.S. Cl. ............... 435/199; 435/6; 435/91.1; 435/252.3; 435/324; 435/410; 435/320.1; 536/23.2

(58) Field of Classification Search ............... 435/199, 435/6, 320.1, 91.1, 252.3, 325, 410; 536/23.2
See application file for complete search history.

(56) References Cited

OTHER PUBLICATIONS

Sirish, M., et al. (2002) J. Inorg. Biochem. 91, 253-258.*
Kovacic, R.T., et al. (2003) J. Am. Chem. Soc. 125, 6656-6662.*
Caravan, P., et al. (2003) Chem. Commun. 21, 2574-2575.*
Bashkin, J.K., et al., "Sequence-Specific Cleavage of HIV mRNA by a Ribozyme Mimic", *J. Am. Chem. Soc.*, 116, pp. 5981-5982, (1994).
Basile, L.A., et al., "Metal-Associated Hydrolytic Cleavage of DNA", *J. Am. Chem. Soc.*, 109, pp. 7550-7551, (1987).
Dixon, N.E., et al., "DNA Hyrdolysis by stable metal complexes", *Chemical Communications*, 11, pp. 1287-1288, (1996).
Fahraeus, R., et al., "New Approaches to Cancer Therapies", *Journal of Pathology*, 187, pp. 138-146, (1999).
Franklin, S., Research proposal entitled "DNA Binding by a New Motif:Transformation of EF-Hands to HTH Motifs", sent as part of applications for faculty positions (1997).
Glover, J.M., et al., "Crystal structure of the heterodimeric bZIP transcription factor c-Fos-c-Jun bound to DNA", *Nature*, 373, pp. 257-261, (1995).
Hashimoto, S., et al., "Characterization Lanthanide-mediated DNA cleavage by intercalator-linked hydroxamic acids: comparison with transition systems", *J. Chem. Soc., Perkin Trans.*, 1, pp. 2623-2628, (1996).
Hayashi, N., et al., "Site-Selective Hydrolysis of tRNA by Lanthanide Metal Complexes", *Inorganic Chemistry*, 32 (26), pp. 5899-5900, (1993).

Hegg, E.L., et al., "Copper(II) Macrocycles Cleave Single-Stranded and Double-Stranded DNA under Both Aerobic and Anaerobic Conditions", *Inorganic Chemistry*, 35 (26), pp. 7474-7481, (1996).
Hettich, R., et al., "Cobalt(III) Polyamine Complexes as Catalysts for the Hydrolysis of Phosphate Esters and of DNA. A Measurable 10 Million-Fold Rate Increase", *J. Am. Chem. Soc.*, 119, pp. 5638-5647, (1997).
Hettich, R., et al., "Supramolecular chemistry. Part 71. Evidence for hydrolytic DNA cleavage by lanthanide(III) and cobalt(III) derivatives", *J. Chem. Soc. Perkin Trans.*, 2, pp. 2069-2072, (1997).
Huang, B., et al., "Splase: A New Class IIS Zinc-Finger Restriction Endonuclease with Specificity for Sp1 Binding Sites", *Journal of Protein Chemistry*, 15 (5), pp. 481-489, (1996).
Itoh, T., et al., "Hydrolytic cleavage of DNA by a novel copper(II) complex with cis,cis-1,3,5-triaminocyclohexane", *Chemical Communications*, 7, pp. 677-678, (1997).
Kanaya, S., et al., "A Hybrid Ribonuclease H: A Novel RNA Cleaving Enzyme with Sequence-Specific Recognition", *The Journal of Biological Chemistry*, 267 (12), pp. 8492-8498, (1992).
Kim, Y., et al., "Chimeric restriction endonuclease", *PNAS*, 91, pp. 883-887, (Feb. 1994).
Kim, Y., et al., "Chimeric Restriction Enzyme: Gal4 Fusion to FokI Cleavage Domain", *Biol. Chem.*, 379, pp. 489-495, (1998).
Kim, Y., et al., "Hybrid restriction enzymes: Zinc finger fusions to Fok I cleavage domain", *PNAS*, 93, pp. 1156-1160, (1996).
Kissinger, C.R., et al., "Crystal Structure of an engrailed Homeodomain-DNA Complex at 2.8 A Resolution: A Framework for Understanding Homeodomain-DNA Interactions", *Cell*, 63, pp. 579-590, (1990).
Klemm, J.D., et al., "Crystal Structure of the Oct-1 POU Domain Bound to an Octamer Site: DNA Recognition with Tethered DNA-Binding Modules", *Cell*, 77, pp. 21-32, (1994).
Komiyama, M., et al., "Cerium(IV)-oligoDNA hybrid as highly selective artificial nuclease", *Supramolecular Chemistry*, 4, pp. 31-34, (1994).
Komiyama, M., et al., "Consecutive Catalysis by Cerium(III) Ion for Complete Hydrolysis of Phosphodiester Linkage in DNA", *Chemistry Express*, 8 (2), pp. 85-88, (1993).
Komiyama, M., et al., "DNA Hydrolysis by Cerium(IV) Does Not Involve either Molecular Oxygen or Hydrogen Peroxide", *Chemistry Letters*, 6, pp. 1025-1028, (1994).
Komiyama, M., et al., "Rare Earth Metal Ions for DNA Hydrolyses and Their Use to Artificial Nuclease", *Nucleosides & Nucleotides*, 13 (6&7), pp. 1297-1309, (1994).

(Continued)

*Primary Examiner*—Charles L. Patterson, Jr.
(74) *Attorney, Agent, or Firm*—Schwegman, Lundberg, Woessner & Kluth, P.A.

(57) ABSTRACT

The present invention provides artificial endonucleases and methods to prepare and use those endonucleases.

32 Claims, 13 Drawing Sheets
(3 of 13 Drawing Sheet(s) Filed in Color)

OTHER PUBLICATIONS

Li, L., et al., "Alteration of the cleavage distance of Fok I restriction endonuclease by insertion mutagenesis", *PNAS*, 90, pp. 2764-2768, (1993).

Li, L., et al., "Functional domains in Fok I restriction endonuclease", *PNAS*, 89, pp. 4275-4279, (1992).

Magda, D., et al., "Site-Specific Hydrolysis of RNA by Europium(III) Texaphyrin Conjugated to a Synthetic Oligodeoxyribonucleotide", *J. Am. Chem. Soc.*, 116, pp. 7439-7440, (1994).

Matsumura, K., et al., "Lanthanide Complex—Oligo-DNA Hybrid for Sequence-selective Hydrolysis of RNA", *Journal of Chemical Society, Chemical Communications*, pp. 2019-2020, (1994).

Ott, R., et al., "DNA hydrolysis by inorganic catalysts", *Applied Microbiology and Biotechnology*, 52 (6), pp. 761-767, (Nov. 1999).

Pomerantz, J.L., et al., "Structure-Based Design of Transcription Factors", *Science*, 267, pp. 93-96, (1995).

Rammo, J., et al., "Ligand and Cosubstrate Effects on the Hydrolysis of Phosphate Esters and DNA with Lanthanoids", *Liebigs Annalen*, pp. 1757-1767, (1996).

Rammo, J., et al., "Supramolecular complexes of transition-metal(II) ions for the hydrolysis of phophate esters and of DNA", *Inorganica Chimica Acta*, 251, pp. 125-134, (1996).

Reynolds, M.A., et al., "Antisense oligonucleotides containing an internal non-nucleotide-based linker promote site-specific cleavage of RNA", *Nucleic Acids Research*, 24 (4), pp. 760-765, (1996).

Roth, J.A., et al., "Gene Therapy for Cancer: What Have We Done and Where Are We Going?", *Journal of the National Cancer Institute*, 89 (1), pp. 21-39, (Jan. 1997).

Sagripanti, J., et al., "Site-specific Oxidative DNA Damage at Polyguanosines Produced by Copper Plus Hydrogen Peroxide", *The Journal of Biological Chemistry*, 264 (3), pp. 1729-1734, (1989).

Schnaith, L.M., et al., "Double stranded cleavage of pBR322 by a Diiron complex via a hydrolytic mechanism", *Proc. Nat. Acad. Sci. USA*, 91, pp. 569-573, (1994).

Schwabe, J.W., et al., "The Crystal Structure of the Estrogen Receptor DNA-Binding Domain Bound to DNA: How Receptors Discriminate between Their Response Elements", *Cell*, 75, pp. 567-578, (1993).

Schwabe, J.W., et al., "Zinc mining for protein domains", *Structural Biology*, 1 (6), pp. 345-349, (1994).

Takenaka, S., et al., "Cleavage of Double Helical DNA by Cu2+ Ion in the Presence of Bisintercalator Containing Penta(ethylene glycol) Connector Chain", *Journal of Molecular Recognition*, 3 (4), pp. 156-162, (1990).

Trawick, B.N., et al., "Inorganic Mimics of Ribonucleases and Ribozymes: From Random Cleavage to Sequence-Specific Chemistry to Catalytic Antisense Drugs", *Chemical Reviews*, 98 (3), pp. 939-960, (1998).

Uchiyama, Y., et al., "DNA-Linked RNase H for Site-Selective Cleavage of RNA", *Bioconjugate Chemistry*, 5 (4), pp. 327-332, (1994).

Vlassov, V., et al., "Sequence-Specific Cleavage of Yeast tRNA-Phe with Oligonucleotides Conjugated to a Diimidazole Construct", *Antisense & Nucleic Acid Development*, 7, pp. 39-42, (1997).

Wolberger, C., et al., "Crystal Structure of a MATapha 2 Honeodomain-Operator Complex Suggests a General Model for Homeodomain-DNA Interactions", *Cell*, 67, pp. 517-528, (1991).

Zhu, B., et al., "Lanthanide binuclear macrocyclic complexes as synthetic enzymes for the cleavage of DNA", *Journal of Molecular Catalysis A: Chemical*, 135, pp. 107-110, (1998).

Zuckerman, R.N., et al., "A Hybrid Sequence-Selective Ribonuclease S", *J. Am. Chem. Soc.*, 110, pp. 6592-6594, (1988).

Zuckermann, R.N., et al., "Site-selective cleavage of structured RNA by a staphylococcal nuclease-DNA hybrid", *PNAS*, 86, pp. 1766-1770, (1989).

Mannervik, M., "Target Genes of Homeodomain Proteins", *BioEssays*, vol. 21, No. 4, pp. 267-270, (Apr., 1999).

Richardson, C.C., et al., "Homeodomain Proteins", *Annual Review of Biochemistry*, vol. 63, pp. 487-526, (1994).

Stein, S., et al., "Checklist: Vertebrate Homeobox Genes", *Mechanisms of Development*, vol. 55, No. 1, pp. 91-108, (Mar., 1996).

Stroud, R.M., et al., "Eukaryotic Transcription Factor-DNA Complexes", *Annual Review of Biophysics and Biomolecular Structure*, vol. 26, pp. 289-325, (1997).

Vollmer, J.Y., et al., "Homeobox Genes in the Developing Mouse Brain", *Journal of Neurochemistry*, vol. 71, No. 1, pp. 1-19, (Jul., 1998).

Wolberger, C., "Homeodomain Interactions", *Current Opinion in Structural Biology*, vol. 6, No. 1, pp. 62-68, (Feb., 1996).

Kim, Y., et al., "Chimeric HTH motifs based on EF-hands", *Journal of Biological Inorganic Chemistry* vol. 6 No. 2, (Feb. 2001), 173-181.

Welch, Joel, et al., "De Nova Nucleases based on HTH and EF-Hand Chimeras", *Inorganic Chemistry* Vo. 40 No. 9, (Apr. 23, 2001), 1982-1984.

Lewit-Bentley A, Rety S., "EF-hand calcium-bing proteins", *National Library of Medicine, Curr Opin Struct Biol.* 10(6), (Dec. 2000),637-643, (abstract only).

Mainguy, Gaell, et al., "Regulation of Epidermal Bullous Pemphigoid Antigen 1 (BPAG1) Synthesis by Homeoprotein Transcription Factors", *The Journal of Investigative Dermatology*, vol. 113, No. 4, (Oct. 1999),643-650.

Pomerantz, Joel L., et al., "Analysis of homeodomain function by structure- based design of a transcription factor", *Proc. Natl. Acad. Sci. USA*, vol. 92, (Oct. 1995),9752-9756.

Pomerantz, J. L., et al., "Structure-Based Design of Transcription Factors", *Science*, 267, (1995),pp. 93-96.

Tejada, Max L., et al., "Determinants of the DNA-Binding Specificity of the Avian Homeodomain Protein, AKR", *DNA and Cell Biology*, vol. 18, No. 10, (1999),791-804.

Zhang M, Yuan T., "Molecular mechanisms of calmodulin's functional versatility", *Biochem Cell Biol.*; 76(2-3), (1998),313-323 (abstract only).

\* cited by examiner

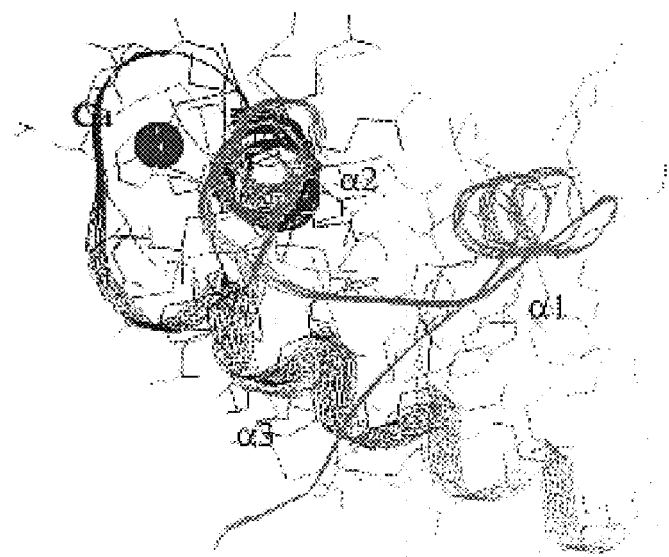
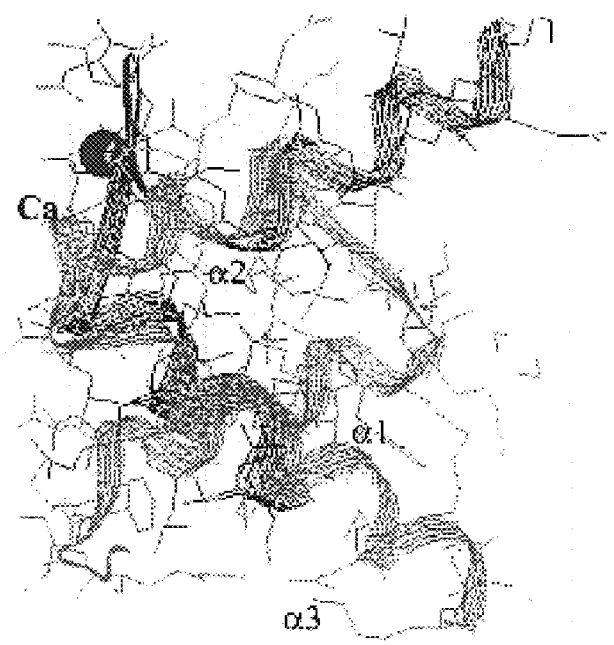
FIG. 1C

P2

N-term–ERRRQQLSSEAETIFGDGDKDEIKIWFQNKRAK–C-term

P3 x  x  x  x x   x

N-term–TERRRQQLDKDGDGTIDEREIKIHFQNKRAKIK–C-term

P3W

N-term–TERRRQQLDKDGDGTIDEREIKIWFQNKRAKIK–C-term

P4

N-term–TERRRFRVFDKDGNGYISAAEKIWFQNKRAKIK–C-term

P4a

N-term–TERRRFDKDGNGYISAAELRHVKIWFQNKRAKIK–C-term

P5

N-term–TRRRRFLSFDKDGDGTITTKEEVWFQNRRMKWK–C-term

CM1

N-term–DEKRPRTAFSGEQLARLKREFNENRYLTERRR
LRVFDKDGNGFISAAEKIWFQNKRAKIKKST–C-term

FIG. 2

ARTIFICIAL ENDONUCLEASE

BACKGROUND OF THE INVENTION

Natural endonucleases have the ability to distinguish and cleave a given DNA sequence with remarkable selectivity, but this level of finesse has not yet been achieved with synthetic small molecule analogs (Truwick et al., 1998; Ott et al., 1999). It is of great interest to generate an artificial endonuclease to target sequences of choice, not only for their biochemical utility, but for the pharmaceutical impact of cleavage agents which could target a single sequence in the genome. Such an agent could serve to regulate transcription of given genes, such as ras, P16, lac or P53 which often go awry in cancers (Fahraeus et al., 1999; Roth et al., 1997), or to down-regulate gene expression for the treatment of genetic disease, inflammation, or infection.

A number of different approaches have been used to prepare artificial nucleases having sequence specificity. One approach is to link a nucleic acid binding domain isolated from one protein to a domain from another protein that exhibits nuclease activity. For example, the FokI endonuclease DNA binding domain (Li et al., 1992; Li et al., 1993) has been fused to the *Drosophila* Ubx homeodomain, to zinc-finger DNA binding domains, and to the yeast Gal4 DNA binding domain (Kim et al., 1994: Kim et al., 1996; Huang et al., 1996; Kim et al., 1998). Another approach is to link an oligonucleotide that binds to a specific nucleotide sequence in a target nucleic acid with the domain of a protein that has nuclease activity. Examples of protein domains that have been used with this type of approach include staphylococcal nuclease, RNase S, and *E. coli* RNase H (Zucherman et al., 1989; Zucherman et al., 1988; Kanaya et al., 1992; Uchiyama et al., 1994).

Metal and organic complexes that cleave nucleic acid have also been linked to oligonucleotides. Examples of metal and organic complexes that have been used to prepare this type of artificial nuclease include a terpyridine group, a lanthanide-complexing iminodiacetate residue, Eu(III) chelated by a pentadentate texaphyrin ligand, imidazole, and histamine groups (Bashkin et al., 1994; Matsumura et al., 1994; Magda et al., 1994; Reynolds et al., 1996; Vlassov et al., 1997).

Basile et al. (1987) report that plasmid DNA was incubated with chelate complexes of non-redox-active metal ions Zn(II) and Cd(II) (e.g., with phenanthroline) to produce nicked DNA. More recently, hydrolysis of supercoiled DNA has also been achieved with Ln(III) complexes (Tanaka et al., 1990; Hayashi et al., 1993; Rammo et al., 1996; Rammo et al., 1996a; Zhu et al., 1998), a dinuclear Fe(III) complex (Schnaith et al., 1994), Co(III) complexes (Dixon et al., 1996; Hettich et al., 1997a), Cu(II) complexes (Hegg et al., 1996; Itoh et al., 1997), and various divalent transition metal ions (Sagripanti et al., 1989; Hashimoto et al., 1996; Rammo et al., 1996b). A dinuclear Co(III) complex was among the most efficient complexes (Hettich et al., 1997b).

Hydrolysis of linear DNA has been achieved with heterogeneous Ce(IV) hydroxide systems which also form in situ from Ce(III) salts and dioxygen (Komiyama et al., 1993a; Tagasaki et al., 1994; Komiyama et al., 1994a, 1994b, 1994c). Redox-active Cu(II) phenanthroline complexes were also able to produce nicked DNA from a supercoiled template. However, in this case T4 DNA ligase was not able to religate the nicked DNA, suggesting that the Cu(II) complexes utilized a mechanism of cleavage other than that used by the other metals described above, i.e., not via hydrolysis.

DNA binding domains are generally small and compact, and so in some instances out of the context of a full length DNA binding polypeptide, the domain may not make a sufficient number of contacts with DNA to specify both a unique target site and bind with reasonable affinity. To overcome this problem, arms or tails that recognize additional features of the DNA have been added to DNA binding domains (Kissinger et al., 1990; Wolberg et al., 1991), or the polypeptide has been engineered to form either homo- or heterodimers (Schwabe et al., 1993; Glover & Harrison, 1995; Schwage et al., 1994; Klemm et al., 1994). One example is the artificial protein ZFHD1 that was constructed by linking two zinc-fingers with a homeodomain (Pomerantz et al., 1995).

Thus, there is a continuing need for an artificial endonuclease that has specificity for a particular nucleic acid sequence.

SUMMARY OF THE INVENTION

The invention provides an artificial (synthetic) endonuclease that exploits the exquisite specificity achieved by DNA binding proteins to deliver a metal to, i.e., in close proximity to, a gene or other nucleotide sequence for selective damage, e.g., the metal binding portion of the artificial endonuclease has catalytic endonuclease activity. Although several groups have been successful in maintaining protein tertiary structure while mutating residues, loops, and even domains, including designing new metal binding functionality into known protein scaffolds (DeGrado et al., 1999; Regan, 1999; Lombardi et al., 2000; Hellinga, 1998; Gibney, et al., 1997), in contrast, the present invention employs a chimeric motif comprising at least two domains, i.e., domains based on those found in proteins in nature ("biological domains" of parent proteins), including a nucleic acid binding domain and a metal binding domain which promotes supersecondary turn structure and has a hydrolytic or redox active site.

In one embodiment of the invention, the synthetic endonuclease is a peptide or a polypeptide. Thus, the DNA binding domain of the parent DNA binding polypeptide, the nucleic acid binding domain of the peptide or polypeptide of the invention, the metal binding domain of the parent metal binding polypeptide and the metal binding domain of the peptide or polypeptide of the invention have similarity (are substantially superimposable) in their helix orientation. Preferably, at least the turn in the DNA binding domain is substantially superimposable with the metal binding domain. For example, crystal structures of loops that bind metals which have about a 90°, e.g., a 85° to 95°, and preferably a 86° to 94°, turn can be compared to crystal structures of DNA binding domains. Thus, the synthetic peptide or polypeptide of the invention has the DNA binding and metal binding properties of its parents, e.g., interacts specifically with a given nucleic acid sequence, has metal-dependent structure, and/or catalyzes phosphate hydrolysis, both of activated phosphate esters and supercoiled duplex DNA. For example, the metal binding domain may comprise a Lewis-acid metal ion binding motif such as a lanthanide-binding motif. Also preferably, the peptide or polypeptide of the invention translocates into cells, localizes in the nucleus, and/or inhibits transcription of the open reading frame. Preferably, the peptide or polypeptide of the invention comprises a helix-turn-helix, a winged helix-turn-helix, a relaxed helix-turn-helix or a helix-loop-strand, wherein the turn or loop specifically binds a metal, e.g., the Ca-binding domain of EF-Hand, the Fe-binding domain of rubridoxin, or the Cu-binding domain of Atx1, a copper chaperone protein.

As described herein, for one synthetic endonuclease, the chimeric motif comprises a transcription factor DNA binding domain comprising the helical regions of a helix-turn-helix (HTH) domain, and a metal binding domain comprising the topologically (i.e., geometrically) equivalent Ca-binding EF-Hand loop motif at the turn. Four 33-residue peptides (P2, P3, P4 and P5) and one 34-residue peptide (P4a) were constructed. P3 (SEQ ID NO:2) includes the 12-residue consensus EF-Hand loop, P2 (control; SEQ ID NO:1) contains the reversed EF-Hand loop sequence, and P4a (SEQ ID NO:3) comprises α2 and α3 of engrailed, minus the last turn of α2 and the β-turn, and calmodulin loop I. P4 (SEQ ID NO:4) incorporates a greater fraction of the EF-Hand turn than P4 and P5 (SEQ ID NO:5) comprises α2 and α3 of the Antennapedia homeodomain and calmodulin loop III.

The Eu(III) and Ca(II) binding properties of P2 and P3 were investigated by circular dichroism and NMR. P3 was 25% helical in its Eu(III)-saturated form, and 14% helical with excess Ca(II). Both the free and Eu-bound peptides had inherent solution structure, as demonstrated by the helicity induced by the addition of trifluoroethanol (TFE) solvent. While Eu(III)-binding stabilized the structure of P3, it destabilized the structure of P2. The NMR titration of P3 with Eu(III) resulted in new resonances characteristic of Ca-bound EF-Hand loops. As observed for isolated EF-Hands, the resonances appear within the first 0.5 equivalents of Eu(III) added, suggesting that one metal ion organizes two equivalents of peptide to fold into the back-to-back dimer structure of native EF-Hands. EuP3, but not EuP2, had significant affinity for supercoiled plasmid DNA, causing a gel shift at concentrations as low as 10 μM EuP3 (50 μM base pairs).

Thus, the invention provides a synthetic endonuclease, e.g., a peptide or polypeptide, comprising a domain which specifically binds a particular nucleic acid sequence and a domain which specifically binds a metal. The nucleic acid binding domain may be any amino acid sequence which specifically binds a nucleic acid sequence, e.g., a sequence present in dsDNA, dsRNA, ssDNA, ssRNA, A-DNA, B-DNA, Z-DNA and the like. The domain which specifically binds the metal is preferably within (embedded in) the domain which specifically binds the nucleic acid sequence. The metal binding domain may bind any metal including but not limited to Ca(II), Eu(III), Zn(II), Cr(IV), Cd(II), Ce(III), Fe(III), Co(III), Cu(II), or analogs thereof, i.e., metals in the same group, and preferably specifically binds a hydrolytic metal. Exemplary synthetic peptides include SEQ ID NO:2, SEQ ID NO:3, SEQ ID NO:4, SEQ ID NO:5, a derivative thereof or an analog thereof.

In one embodiment, the synthetic peptide or polypeptide comprises a parental helix-turn-helix motif where the turn and optionally a portion of the first helix in the synthetic peptide or polypeptide is a domain which specifically binds a metal, e.g., SEQ ID NO:3, or a catalytically active portion (fragment) thereof. In another embodiment, the synthetic peptide or polypeptide comprises a parental helix-turn-helix motif where the turn in the synthetic peptide or polypeptide is a loop from a helix-loop-strand domain which specifically binds a metal, e.g., the DNA binding domain of a transcription factor and the metal binding domain of a polypeptide such as Atx1, which binds $Cu^{2+}$. A peptide or polypeptide of the invention comprises at least 20, preferably at least 30, up to 50 or more, e.g., 250, 500 or 1000 or more, residues in length. A peptide is generally less than 50 residues in length.

The invention also provides a method for preparing artificial endonucleases. The method comprises identifying a secondary structure in a first molecule, e.g., an amino acid sequence, that specifically binds to a specific nucleic acid sequence and which has similarity to the secondary structure of a second molecule, e.g., an amino acid sequence, that specifically binds a metal and has a hydrolytic or redox active site. Based on a comparison of these molecules, a synthetic (third) molecule is identified which comprises a portion of each of the two parent molecules and which specifically binds the nucleic acid sequence and the metal. The synthetic molecule may be prepared by any means, e.g., for peptides or polypeptides by chemical synthetic means or recombinant means.

The present invention also provides an expression cassette encoding a synthetic endonuclease of the invention. An expression cassette of the invention comprises a promoter functional in a host cell, e.g., in a plant, microbe, or animal including a mammal such as a human, operably linked to a nucleic acid molecule encoding the synthetic endonuclease, i.e., synthetic peptide or polypeptide. In one embodiment, the genome of the host cell does not comprise the nucleic acid sequence recognized by the nucleic acid binding portion of the synthetic peptide or polypeptide or that sequence is modified, e.g., methylated, so that the sequence is not recognized by the nucleic acid binding portion of the synthetic peptide or polypeptide. The expression cassette can also comprise an antisense sequence for the synthetic peptide or polypeptide. In one preferred embodiment, the expression cassette is introduced in a vector for expression in bacteria, e.g., E. coli. The invention also provides a host cell transfected or transformed with the expression cassette, and peptide or polypeptide of the invention isolated from the host cell. Alternatively, the transcription and/or translation of the open reading frame in the expression cassette to yield a synthetic peptide or polypeptide may occur in an in vitro system. The invention further provides an isolated nucleic acid molecule encoding the peptide or polypeptide of the invention.

Another embodiment of the invention provides a method of using the synthetic endonuclease of the invention, e.g., in a cell-free assay. The method comprises contacting a sample comprising isolated nucleic acid which is suspected of having at least one copy of a nucleic acid sequence to which the synthetic endonuclease specifically binds, with an amount of the synthetic endonuclease effective to cleave at least one strand of the nucleic acid sequence. Then cleavage is detected or determined. In another embodiment, the amount of the synthetic peptide or polypeptide of the invention is effective to bind to the nucleic acid sequence and prevent or repress transcription of adjacent sequences after the peptide or polypeptide binds the metal.

Further provided is a method in which the synthetic endonuclease is contacted with a cell. The synthetic endonuclease of the invention may be delivered to a cell via any means, for example, in a liposome, as a conjugate or a fusion polypeptide, e.g., conjugated or recombinantly fused to a peptide transport domain (PTD) such as the TAT peptide (see, for example, Schwarze et al., 2000; Schwarze et al., 1999; Gius et al., 1999; Lindgren et al., 2000; Derossi et al., 1998; Drochiantz, 1999), HSV VP22 or α3 of homeodomains such as Antennapedia α3, or in a vector, e.g., a viral vector, or in the absence of additional PTD as certain domains in the nucleic acid binding domain, e.g., α3 of engrailed, may be a PTD. Then it is determined whether the synthetic endonuclease has cleaved at least one strand of the nucleic acid sequence in the genome of the cell.

The invention further provides a therapeutic method of treating a disease such as cancer. For example, a mammal in need of such treatment is contacted with a synthetic endonuclease of the invention, e.g., one linked to a PTD or an antibody that specifically binds to an epitope specific for a particular cell such as a cancer cell, in an amount effective to treat the disease. For example, to treat cancer a conjugate which comprises the peptide or polypeptide of the invention linked to an antibody, e.g., polyclonal, monoclonal, single-chain antibody, a chimeric or humanized antibody, or a fragment thereof which specifically binds to a cancer cell-specific epitope, is administered to the mammal having cancer in an amount effective to inhibit or prevent proliferation of malignant cells. Thus, for a mammal having a cancer associated with aberrant expression of P16, lac or P53, the mammal is administered a synthetic endonuclease of the invention conjugated to an antibody that specifically binds to the cancer cells and, once the synthetic endonuclease enters the nucleus of the cancer cell, specifically binds to the nucleic acid sequence which corresponds to P16, lac or P53. In another embodiment, an expression cassette of the invention is introduced to the mammal in an amount effective to treat a particular disease.

The synthetic endonuclease of the invention is also useful as a biological probe, e.g., to knock out gene function temporally, e.g., for otherwise lethal mutations, or spatially, and to study developmental cascades of gene function. The synthetic endonuclease is further useful as a conformational probe, to prepare sequence-specific endonucleases, e.g., restriction enzymes, for molecular biology applications, and as an agent to block or inhibit transcription for clinical antibiotic and chemotherapy applications. In this embodiment, a hydrolytic rather than oxidative cleavage mechanism is desirable for several reasons. Oxidative cleavage of DNA and RNA produces diffusible free radicals. For molecular biology applications, this results in strand ends that cannot be enzymatically religated, and for clinical applications, oxidative cleavage can cause indiscriminant peripheral damage to the cell.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1C. Two views of the overlay of engrailed (1ENH) helix-turn-helix (HTH) region ($\alpha 2$-$\alpha 2$) and one EF-hand of calmodulin (1OSA; third Ca-site) thus illustrating that the helices occupy the same space. The C-terminal $\alpha 3$ is the homeodomain recognition helix which binds in the DNA major grove. $\alpha 1$, $\alpha 2$ and $\alpha 3$ of Engrailed (1ENH; in blue) are shown and calmodulin (1OSA; third Ca-sitein; purple) is shown binding a metal. The Ca(II) ion is shown as a solid red sphere.

FIG. 2. Sequences of peptide P2 (control; SEQ ID NO:1) P3, P4, P4a and P5 (synthetic; SEQ ID NO:2, SEQ ID NO:7, SEQ ID NO:4, SEQ ID NO:3 and SEQ ID NO:5, respectively), and loop modified Engrailed (SEQ ID NO:6). Parent protein sequence is indicated by double or single underlining (homeodomain and EF-hand). Expected sites of Ca(II) and Eu(III) binding are indicated by an x and the 12 residues of the Ca-binding loop are shaded.

DETAILED DESCRIPTION OF THE INVENTION

Definitions

Figure 1A:
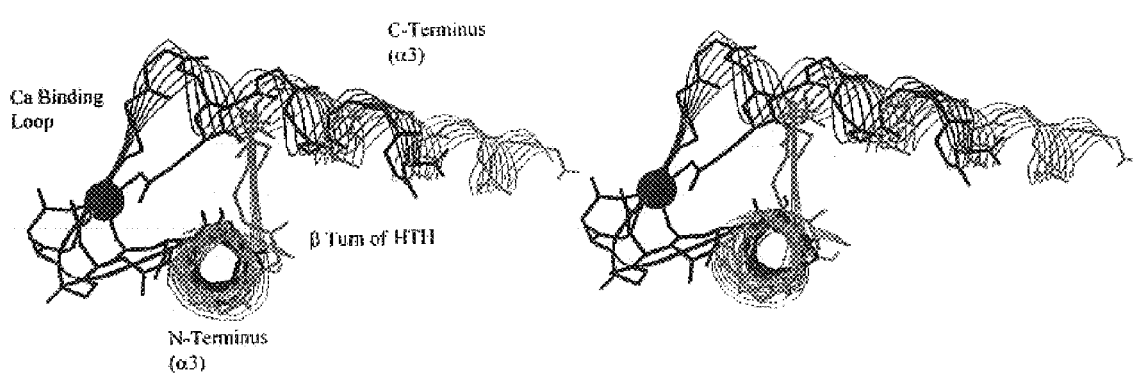
FIG. 1A. Stereo view of the overlay of engrailed HTH region ($\alpha 2$-$\alpha 3$; 1ENH; in green) and one EF-Hand of parvalbumin (5PAL; in blue), to illustrate that the helical axes are colinear. The C-terminal $\alpha 3$ is the homeodomain DNA-recognition helix. Engrailed is shown from the lower center, directly up and then to the righe; parvalbumiun is shown from the lower center to the lower left, then upwards and finally to the right; and the Ca(II) ion is shown as a solid magenta sphere having lines extended therefrom representing its ligands.

The term "antibody" as used herein means a portion of an immunoglobulin molecule (see Paul, 1984) capable of binding to an antigen. According to this definition, the term "antibody" includes various forms of modified or altered antibodies, such as an intact immunoglobulin, an Fv fragment containing only the light and heavy chain variable regions, an Fab or (Fab)'$_2$ fragment containing the variable regions and parts of the constant regions, a single-chain antibody (Bird et al., 1988; Huston et al., 1988,), and the like. The antibody may be of animal (especially mouse or rat) or human origin or may be chimeric (Morrison et al., 1984) or humanized (Jones et al., 1986 and UK patent application 8707252).

An "artificial or synthetic endonuclease" as used herein is preferably a peptide or polypeptide, or an analog or a derivative thereof, which specifically binds to nucleic acid and specifically binds a metal and comprises an amino acid sequence which is not found in nature. Preferably, the artificial or synthetic endonuclease comprises an amino acid sequence comprising a domain that specifically binds to a particular nucleic acid sequence and a domain which specifically binds a metal and has a hydrolytic or redox active site. More preferably, the artificial or synthetic endonuclease specifically binds to and cleaves at least one strand in the particular nucleic acid sequence.

A "peptide or polypeptide" includes any molecule having two or more natural or unnatural amino acids linked together, either D or L amino acids, including a peptide or polypeptide which is subjected to chemical modifications, such as esterification, amidation, reduction, protection and the like ("derivatives"). Other "derivatives" of the invention include branched peptides, circular branched and branched circular peptides.

An "analog" of a peptide or polypeptide of the invention is a molecule that mimics the activity of that peptide or polypeptide but which is not a peptide or polypeptide or a derivative thereof. As used herein, the term "mimics" means that the molecule has a similar activity to that of a peptide or polypeptide of the invention, but that the activity of the analog is not necessarily of the same magnitude as the activity of the peptide or polypeptide.

It is also envisioned that the peptides, polypeptides, derivatives and analogs thereof of the invention may comprise moieties other than the portions which bind a nucleic acid sequence or bind a metal, such as an antibody or a fragment thereof, a fusion protein, nucleic acid molecules, sugars, lipids, fats, a detectable signal molecule such as a radioisotope, e.g., gamma emitters, paramagnetic molecules or sound wave emitters, small chemicals, metals other than those that bind to the peptide, polypeptide, derivative or analog thereof of the invention, salts, synthetic polymers, e.g., polylactide and polyglycolide, surfactants and glycosaminoglycans, which preferably are covalently attached or linked to the peptide, polypeptide, derivative, or analog thereof, of the invention so that the other moiety does not alter the activity of the peptide, polypeptide, derivative or analog thereof. Also envisioned is a peptide, polypeptide, derivative or analog thereof that is non-covalently associated with the moieties described above.

Preferably, the peptides, polypeptides, derivatives, or analogs thereof of the invention are biologically active. The biological activity can be measured by methods known to the art, some of which are described hereinbelow. For example, a peptide or polypeptide of the invention specifically binds to a nucleic acid sequence and specifically binds a metal, and more preferably cleaves a nucleic acid molecule comprising at least one of the nucleic acid sequences to which the peptide or polypeptide specifically binds.

A "lanthanide" means cerium, praseodymium, neodymium, promethium, samarium, europium, gadolinium, terbium, dysprosium, holmium, erbium, thulium, ytterbium, or lutetium.

"Nuclease activity" includes cleavage of dsDNA, ssDNA, dsRNA, ssRNA, and DNA/RNA duplexes.

An "isolated" nucleic acid molecule, peptide or polypeptide refers to in vitro preparation, isolation and/or purification of a nucleic acid molecule, peptide, or polypeptide of the invention, so that it is not associated with in vivo substances or other molecules present in an in vitro synthesis. Thus, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. An isolated nucleic acid molecule means a polymeric form of nucleotides of at least 10 bases in length, either ribonucleotides or deoxynucleotides or a modified form of either type of nucleotide. The term includes single and double stranded forms of DNA. The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of an expression cassette. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phophoroselenoate, phosphorodiselenoate, phosphoroanilothioate, phosphoroaniladate, phosphoroamidate, and the like. An oligonucleotide can include a label for detection, if desired.

The term "isolated polypeptide" means a polypeptide encoded by cDNA or recombinant RNA, or is synthetic origin, or some combination thereof, which isolated polypeptide (1) is not associated with proteins found in nature, (2) is free of other proteins from the same source, e.g., free of human proteins, (3) is expressed by a cell from a different species, or (4) does not occur in nature.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of one sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

The term "selectively hybridize" means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest is at least 65%, and more typically with preferably increasing homologies of at least about 70%, about 90%, about 95%, about 98%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff (1972). The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) by the homology alignment algorithm of Needleman and Wunsch (1970) by the search for similarity method of Pearson and Lipman (1988) by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20–50 nucleotides, wherein the percentage of sequence identity is calculated by comparing the reference sequence to the polynucleotide sequence which may include deletions or additions which total 20 percent or less of the reference sequence over the window of comparison.

As applied to the sequence of a peptide or a polypeptide, the term "substantial identity" means that two peptide or polypeptide sequences, when optimally aligned, such as by the programs GAP or BESTFIT using default gap weights, share at least about 80 percent sequence identity, preferably at least about 90 percent sequence identity, more preferably at least about 95 percent sequence identity, and most preferably at least about 99 percent sequence identity.

As used herein, the terms "label" or "labeled" refer to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides are known in the art and may be used. Examples of labels for polypeptides include, but are not limited to, the following: radioisotopes (e.g., $^3$H, $^{14}$C, $^{35}$S, $^{125}$O, $^{131}$I), fluorescent labels (e.g., FITC, rhodamine, lanthanide, phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

I. Preparation of Peptides and Polypeptides and Nucleic Acid Molecules of the Invention In one embodiment of the invention, the three-dimensional structure of a polypeptide that specifically binds nucleic acid and another polypeptide which specifically binds a metal are compared. The comparison may include a visual inspection or computer analysis of the three-dimensional structures including but not limited to crystal structures such as those available in the Swiss Protein Data Bank and NMR structures. The sequences of nucleic acid binding domains and metal binding domains that have geometric similarity (e.g., Efimov, 1994; Efimov, 1997; Richardson et al., 1992) are selected to prepare synthetic peptides or polypeptides. Preferably, the metal binding domain is introduced into, or in place of, a region of the nucleic acid binding domain that is not required for binding to nucleic acid, e.g., a region that links two regions of the nucleic acid binding domain that bind nucleic acid. Additional residues may be deleted or inserted in either or both domains, or certain residues may be substituted to enhance the nucleic acid binding, metal binding, stability, catalytic, affinity for other proteins, membrane translocation, or biodistribution properties of the synthetic peptide or polypeptide.

A. Nucleic Acid Molecules

1. Expression Cassettes

To prepare expression cassettes for transformation herein, the recombinant DNA sequence or segment encoding the peptide or polypeptide of the invention may be circular or linear, double-stranded or single-stranded. A DNA sequence which encodes an RNA sequence that is substantially complementary to a mRNA sequence is typically a "sense" DNA sequence cloned into a cassette in the opposite orientation (i.e., 3' to 5' rather than 5' to 3'). Generally, the recombinant DNA sequence or segment is in the form of chimeric DNA, such as plasmid DNA, that can also contain coding regions flanked by control sequences which promote the expression of the DNA present in the resultant host cell.

As used herein, "chimeric" nucleic acid means that a vector comprises DNA from at least two different species, is synthetic or comprises DNA from the same species which is linked or associated in a manner which does not occur in the "native" or wild type of the species.

Aside from DNA sequences that serve as transcription units, a portion of the recombinant DNA may be untranscribed, serving a regulatory or a structural function. For example, the DNA may itself comprise a promoter that is active in prokaryotic or eukaryotic cells such as mammalian cells, or may utilize a promoter already present in the genome that is the transformation target.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the recombinant DNA has been introduced into the recipient cells.

The general methods for constructing recombinant DNA which can transform target cells are well known to those skilled in the art, and the same compositions and methods of construction may be utilized to produce the DNA useful herein. For example, Sambrook et al. (1989), provides suitable methods of construction.

2. Transformation into Host Cells

The recombinant DNA can be readily introduced into the host cells, e.g., mammalian, bacterial, yeast or insect cells by transfection with an expression vector comprising DNA or its complement, by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell.

Physical methods to introduce a recombinant DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian gene therapy, it is desirable to use an efficient means of precisely inserting a single copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell may be of mammalian origin or of non-mammalian origin, including plant, insect, yeast, fungal or bacterial sources.

"Transfected" or "transformed" is used herein to include any host cell or cell line, the genome of which has been altered or augmented by the presence of at least one recombinant DNA sequence, which DNA is also referred to in the art of genetic engineering as "heterologous DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular endonuclease, e.g., by immunological means (ELISAs and Western blots) or by assays described herein to identify molecules falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the recombinant DNA segment is being expressed. Expression may be evaluated by specifically identifying the peptide products of the introduced preselected DNA sequences or evaluating the phenotypic changes brought about by the expression of the introduced recombinant DNA segment in the host cell.

B. Peptides and Polypeptides

The present isolated peptides or polypeptides can be synthesized in vitro, e.g., by the solid phase peptide synthetic method or by recombinant DNA approaches (see above). The solid phase peptide synthetic method is an established and widely used method, which is described in the following references: Stewart et al. (1969); Merrifield (1963); Meienhofer (1973); Bavaay and Merrifield, (1980); and Clark-Lewis et al. (1997). These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, can be readily prepared. For example, amides of the peptide or polypeptide of the present invention may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a peptide or polypeptide of the invention may be prepared in the usual manner by contacting the peptide or polypeptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the peptide or polypeptide may be prepared by utilizing an N-acyl protected amino acid for the final condensation, or by acylating a protected or unprotected peptide or polypeptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the peptide. Other amino-terminal modifications include aminooxypentane modifications (see Simmons et al., 1997).

In addition, the amino acid sequence of a peptide or polypeptide can be modified so as to result in a peptide or polypeptide variant. The modification includes the substitution of at least one amino acid residue in the peptide for another amino acid residue, including substitutions which utilize the D rather than L form, as well as other well known amino acid analogs, e.g., unnatural amino acids such as $\alpha$, $\alpha$-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, $\alpha$-methyl-alanine, para-benzoyl-phenylalanine, phenylglycine, propargylglycine, sarcosine, $\epsilon$-N,N,N-trimethyllysine, $\epsilon$-N-acetyllysine, N-acetylserine, N-formylmethionine, 3-methylhistidine, 5-hydroxylysine, $\omega$-N-methylarginine, and other similar amino acids and imino acids and tert-butylglycine.

One or more of the residues of the peptide or polypeptide of the invention can be altered, so long as the variant peptide or polypeptide is biologically active, i.e., specifically binds nucleic acid and a hydrolytic metal. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional peptide or polypeptide can readily be determined by assaying the activity of the peptide or polypeptide variant.

Amino acid substitutions falling within the scope of the invention, are, in general, accomplished by selecting substitutions that do not differ significantly in their effect on maintaining (a) the structure of the peptide or polypeptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions peptide or polypeptide variants with non-conservative substitutions. Non-conservative substitutions entail exchanging a member of one of the classes described above for another.

Acid addition salts of amino residues of the peptide or polypeptide may be prepared by contacting the peptide or amine with one or more equivalents of the desired inorganic or organic acid, such as, for example, hydrochloric acid. Esters of carboxyl groups of the peptides or polypeptides may also be prepared by any of the usual methods known in the art.

Peptide or polypeptide analogs have properties analogous to those of the corresponding peptide. These analogs can be referred to as "peptide mimetics" or "peptidomimetics" (Fauchere (1986); Veber and Freidinger (1985); and Evans et al. (1987)) and can be developed with the aid of computerized molecular modeling. These analogs include structures having one or more peptide linkages optionally replaced by a linkage selected from the group consisting of: —Ch$_2$NH—, —CH$_2$S—, —CH$_2$—CH$_2$—, —CH=CH-(cis and trans), —CH=CF-(trans), —CoCH$_2$—, —CH(OH)CH$_2$—, and —CH$_2$SO—, by methods known in the art and further described in the following references: Spatola (1983); Spatola (1983); Morley (1980); Hudson (1979) (—CH$_2$NH—, CH$_2$CH$_2$—); Spatola (1986) (—CH$_2$—S); Hann (1982) (—CH=CH—, cis and trans); Almquist (1980) (—COCH$_2$—); Jennings-White et al. (1982) (—COCH$_2$—); EP 45665 (—CH(OH)CH$_2$—); Holladay et al. (1983) (—C(OH)CH$_2$—); and Hruby (1982) (—CH$_2$S—). A particularly preferred non-peptide linkage is —CH$_2$NH—. Such analogs may have greater chemical stability, enhanced pharmacological properties (half-life, absorption, potency, efficacy, etc.), altered specificity (e.g., a broad-spectrum of biological activities), reduced antigenicity, and be economically prepared. Labeling of analogs usually involves covalent attachment of one or more labels, directly or through a spacer (e.g., an amide group), to non-interfering positions(s) on the analog that are predicted by quantitative structure-activity data and/or molecular modeling. Such non-interfering positions generally are positions that do not form direct contacts with the macromolecule(s) to which the analog specifically binds to produce the desired effect. Systematic substitution of one or more amino acids of a consensus sequence with a D-amino acid of the same type (e.g., D-lysine in place of L-lysine) may also be used to generate more stable peptides.

D. Identification of Synthetic Molecules Falling within the Scope of the Invention Once a synthetic molecule is prepared, it may be characterized by methods well known to the art including: 1) comparing the structural similarity of the synthetic molecule to the parent motifs, e.g., comparing the $\alpha$-helicity of the molecule as a function of metal using CD, the solution structure and folding dynamics in the presence of the metal via 1D- and 2D-NMR and X-ray crystallography, and specific molecule-DNA interactions by NMR and X-ray crystallography; 2) determining the affinity of the synthetic molecule for metals, dimerization, and DNA binding, for example, determining the binding affinity of the metal, equilibrium dialysis, CD thermal melt and calorimetric titrations as a function of metal, and determining the kinetics and thermodynamics of dimerization by 1D-NMR titrations, centrifugal sedimentation, and CD denaturation studies, while PAGE gel-shift and footprinting assays are employed with $^{32}$P-labeled DNA for DNA binding and binding constant determinations; 3) measuring the hydrolytic activity of the synthetic molecule bound to the metal, e.g., via cleavage kinetics and catalytic turnover toward phosphate model compounds, oligonucleotide fragments, and plasmids as well as the cleavage dependence on correct fold, recognition helix sequence, and metal ion using an agarose gel assay; 4) establishing the sites of DNA binding and cleavage by the metallomolecule such as metallopeptide or metallopolypeptide by, for example, gel-shift assays of $^{32}$P-radiolabeled DNA as a function of metallopeptide or metallopolypeptide to quantify DNA binding, sequencing gel electrophoresis footprinting assays as a function of metal binding are employed to determine the specificity of the peptide or polypeptide/DNA interaction and the relative selectivity of the synthetic peptide or polypeptide is compared to the parent transcription factors; and 5) targeting DNA sequences of choice and defining the extent of sequence specificity, e.g., the sequence specificity of the DNA cleavage is determined by gel electrophoresis of $^{32}$P-radiolabeled oligonucleotides and cleavage products identified by gel or HPLC analysis.

For peptides or polypeptides, in particular, for 1), the α-helicity, β-sheet, and random coil content can be estimated from the molar ellipticity between 200 and 230 nm. The secondary fold is studied by NMR to determine the solution structure and dynamics in the presence of metals. 2D-NOESY-COSY, and TOCSY experiments in $D_2O$ and 90:10 $H_2O:D_2O$ are employed to assign peaks, from which both local 2° structure and fall 3D-solution structures can be calculated. Further, the effect of the Ca-binding loop structure and sequence on the overall peptide or polypeptide fold is assessed by selected residue modifications coupled to these structural studies.

For 2), lanthanide-binding and dimerization constants ($K_d$ and $K_{dim}$) are determined in several ways. PAGE gel-shift assays and centrifugal sedimentation allow the $K_{dim}$ to be determined. Isothermal titration microcalorimetry is used to determine binding affinities and the thermodynamics of peptide or polypeptide dimerization and self-assembly by quantifying heat releases with the addition of aliquots of metal. Alternately, equilibrium dialysis of solutions of varying Ln/peptide or polypeptide ratios and $K_{dim}$ can be determined. Substitutions in the loop metal-binding residues may also be made to further determine metal affinities. The amount of stabilization afforded the peptide or polypeptide by metal binding is also investigated by CD thermal denaturation studies. In the presence and absence of metal, changes in the CD as a function of temperature can be correlated to thermodynamic parameters. In addition to these studies, Eu(III) and Tb(III) binding constants and the number of inner sphere water molecules can be determined for the peptide or polypeptide bound to Ln by luminescence titrations.

To test hydrolytic activity, the hydrolysis of binitrophenylphosphate (BNPP) is followed. The absorbance increase at 400 nm is due to liberated 4-nitrophenolate which can be monitored over time to give rate constants. The rate reflects the relative accessibility and reactivity of the active site, and can be compared to the rates observed for the hydrolytically active peptide or polypeptide.

Agarose gel assays of supercoiled plasmids are used to screen whether DNA is cut in a metallopeptide or metallopolypeptide-dependent manner, prior to more detailed oligonucleotide assays. The agarose assay also shows whether the synthetic molecules promote single or double strand breaks. The cleavage observed may be random, or may be site specific and peptide or polypeptide dependent. The cleavage dependence on correct fold, recognition helix sequence, and metal, e.g., Ln(III), ion is investigated by gel electrophoresis of $^{32}$P-radiolabeled oligonucleotides (20–200 b.p.). Gel studies establish the specificity toward the targeted DNA sequences, and whether that site specificity is related to the parent nucleic acid binding consensus sequence. Additionally, it is determined whether there are multiple sites of cleavage and their relative affinities, and whether cleavage is strand-specific for a given recognition site (3' vs. 5' strand, or both).

For 4), the thermodynamics of DNA binding is investigated by gel-shift and footprinting assays of $^{32}$P-radiolabeled DNA as a function of metalated peptide or polypeptide. Oligonucleotides are $^{32}$P-labeled for acrylamide gel electrophoresis, and binding gels are quantified using Molecular Dynamics PhosphorImager technology. Both restriction fragments (for sequence screening) and smaller synthesized oligonucleotides are designed to contain the target sequences of the parent nucleic acid binding domain.

For 5), the cleavage observed may be random, or site specific and peptide- or polypeptide-dependent. The specificity of the metalated peptide or polypeptide DNA interaction, e.g., what the target sequence is and how that compares to the target sequence of the parent nucleic acid binding sequence, is determined by gel electrophoresis of $^{32}$P-radiolabeled oligonucleotides. The cleavage products, and thus a hydrolytic mechanism, is verified by comparing fragments to sequencing lanes with both phosphate and hydroxyl termini.

E. Targeting of the Synthetic Molecule of the Invention

Synthetic molecules may be targeted to a specific therapeutic site by linking the molecule to a moiety that specifically binds to a cellular component, e.g., antibodies or fragments thereof, lectins, transferrin (for liver targeting), or other targeting molecules, and small molecule drugs, so as to form a conjugate, i.e., via chemical coupling, or a fusion polypeptide, i.e., via recombinant expression. Targeting of the molecule of the invention can result in increased concentration of the molecule at a specific anatomic location. Moreover, the linking of a molecule to such a binding moiety may increase the stability of the molecule in vivo.

To prepare immunoconjugates useful for targeting a malignant or virus-infected cell, an antibody or fragment thereof having a specificity for a surface antigen on a malignant cell or virus-infected is, in one embodiment, attached to a peptide or polypeptide of the invention. Preferably, a peptide or polypeptide is attached via peptide bonds to the carboxy termini regions, e.g., CH3, of antibody heavy chains. The immunoconjugates can be prepared by genetic engineering techniques, i.e, by forming a nucleic acid construct encoding the immunoconjugate. Preferably, the gene construct encoding the immunoconjugate includes, in 5' to 3' orientation, a DNA segment which encodes a heavy chain variable region, a DNA segment encoding the heavy chain constant region, and a DNA segment coding for the peptide or polypeptide. The fused gene is inserted into an expression vector for transfection of the appropriate recipient cells where it is expressed. The hybrid chain can be combined with a light (or heavy) chain counterpart to form monovalent and divalent immunoconjugates.

The heavy chain constant region for the conjugates can be selected from any of the five isotypes: alpha, delta, epsilon, gamma or mu. Heavy chains or various subclasses (such as the IgG subclasses 1–4) can be used. The light chains can have either a kappa or lambda constant chain. DNA sequences for these immunoglobulin regions are well known in the art (see, e.g., Gillies et al. (1989)).

In preferred embodiments, the variable region is derived from an antibody specific for the target antigen (an antigen associated with a diseased cell such as a cancer cell or virus-infected cell), and the constant region includes the CH1, CH2 and CH3 domains. The gene encoding the peptide or variant is joined, e.g., by appropriate linkers, e.g., by DNA encoding $(Gly_4\text{-}Ser)_3$ in frame to the 3' end of the gene encoding the constant region (e.g., CH3 exon), either directly or through an intergenic region. In certain embodiments, the intergenic region can comprise a nucleotide sequence coding for a proteolytic cleavage site. This site, interposed between the immunoglobulin and the peptide or polypeptide, can be designed to provide for proteolytic release of the peptide or polypeptide at the target site. For example, it is well known that plasmin and trypsin cleave after lysine and arginine residues at sites that are accessible to the proteases. Many other site-specific endoproteases and the amino acid sequences they attack are well known.

The nucleic acid construct can include the endogenous promoter and enhancer for the variable region-encoding gene to regulate expression of the chimeric immunoglobulin chain. For example, the variable region encoding genes can be obtained as DNA fragments comprising the leader peptide, the VJ gene (functionally rearranged variable (V) regions with joining (J) segment) for the light chain or VDJ gene for heavy chain, and the endogenous promoter and enhancer for these genes. Alternatively, the gene coding for the variable region can be obtained apart from endogenous regulatory elements and used in an expression vector which provides these elements.

Variable region genes can be obtained by standard DNA cloning procedures from cells that produce the desired antibody. Screening of the genomic library for a specific functionally rearranged variable region can be accomplished with the use of appropriate DNA probes such as DNA segments containing the J region DNA sequence and sequences downstream. Identification and confirmation of correct clones are then achieved by DNA sequencing of the cloned genes and comparison of the sequence to the corresponding sequence of the full length, properly spliced mRNA.

Genes encoding appropriate variable regions can be obtained generally from Ig-producing lymphoid cells. For example, hybridoma cell lines producing Ig specific for tumor associated antigens or viral antigens can be produced by standard somatic cell hybridization techniques. These Ig-producing cell lines provide the source of variable region genes in functionally rearranged form. The variable region genes are typically of murine origin because the murine system lends itself to the production of a wide variety of Igs of desired specificity.

The DNA fragment containing the functionally rearranged variable region gene is linked to a DNA fragment containing the gene encoding the desired constant region (or a portion thereof). Ig constant regions (heavy and light chain) can be obtained from antibody-producing cells by standard gene cloning techniques. Genes for the two classes of human light chains and the five classes of human heavy chains have been cloned, and thus, constant regions of human origin are readily available from these clones.

The fused gene encoding the hybrid IgH chain is assembled or inserted into expression vectors for incorporation into a recipient cell. The introduction of gene construct into plasmid vectors can be accomplished by standard gene splicing procedures.

The chimeric IgH chain can be co-expressed in the same cell with a corresponding L chain so that a complete immunoglobulin can be expressed and assembled simultaneously. For this purpose, the heavy and light chain constructs can be placed in the same or separate vectors.

Recipient cell lines are generally lymphoid cells. The preferred recipient cell is a myeloma (or hybridoma). Myelomas can synthesize, assemble, and secrete immunoglobulins encoded by transfected genes and they can glycosylate polypeptide. A particularly preferred recipient cell is the Sp2/0 myeloma which normally does not produce endogenous immunoglobulin. When transfected, the cell will produce only Ig encoded by the transfected gene constructs. Transfected myelomas can be grown in culture or in the peritoneum of mice where secreted immunoconjugate can be recovered from ascites fluid. Other lymphoid cells such as B lymphocytes can be used as recipient cells.

There are several methods for transfecting lymphoid cells with vectors containing the nucleic acid constructs encoding the chimeric Ig chain. A preferred way of introducing a vector into lymphoid cells is by spheroblast fusion (see Gillies et al. (1989)). Alternative methods include electroporation or calcium phosphate precipitation.

Other useful methods of producing the immunoconjugates include the preparation of an RNA sequence encoding the construct and its translation in an appropriate in vivo or in vitro system.

Methods for purifying recombinant immunoglobulins are well known. For example, a well known method of purifying antibodies involves protein A purification because of the propensity of protein A to bind the Fc region of antibodies. The antigen binding activity of the purified immunoconjugates can then be measured by methods well known to the art, such as described in Gillies et al. (1989). For example, immunoconjugate activity can be determined using antigen-coated plates in either a direct binding or competition assay format.

In particular, it is preferred that humanized antibodies are prepared and then assayed for their ability to bind antigen. Methods to determine the ability of the humanized antibodies to bind antigen may be accomplished by any of numerous known methods for assaying antigen-antibody affinity.

Humanized antibodies (or fragments thereof) are useful tools in methods for therapeutic purposes. When determining the criteria for employing humanized antibodies or antibody conjugates for in vivo administration for therapeutic purposes, it is desirable that the general attainable targeting ratio is high and that the absolute dose of therapeutic agent delivered to the tumor is sufficient to elicit a significant tumor response. Methods for utilizing the humanized antibodies can be found, for example, in U.S. Pat. Nos. 4,877,868, 5,175,343, 5,213,787, 5,120,526, and 5,202,169.

It will be recognized that the inventors also contemplate the utility of human monoclonal antibodies or "humanized" murine antibody as a vascular smooth muscle binding protein in the therapeutic conjugates of their invention. For example, murine monoclonal antibody may be "chimerized" by genetically recombining the nucleotide sequence encoding the murine Fv region (i.e., containing the antigen binding sites) with the nucleotide sequence encoding a human constant domain region and an Fc region, e.g., in a manner similar to that disclosed in European Patent Application No. 0,411,893 A2. Humanized vascular smooth muscle binding partners will be recognized to have the advantage of decreasing the immunoreactivity of the antibody or polypeptide in the host recipient, which may thereby be useful for increasing the in vivo half-life and reducing the possibility of adverse immune reactions. See also, N. Lonberg et al. (U.S. Pat. Nos. 5,625,126; 5,545,806; and 5,569,825); and Surani et al. (U.S. Pat. No. 5,545,807).

Methods useful to prepare antibody-peptide conjugates are well known to the art. See, for example U.S. Pat. No. 5,650,150, the disclosure of which is incorporated by reference herein. Representative "coupling" methods for linking the peptide or polypeptide, or nucleic acid molecule of the invention, through covalent or non-covalent bonds to the targeting moiety include chemical cross-linkers and heterobifunctional cross-linking compounds (i.e., "linkers") that react to form a bond between reactive groups (such as hydroxyl, amino, amido, or sulfhydryl groups) in the peptide, polypeptide or nucleic acid molecule and other reactive groups (of a similar nature) in the targeting moiety. This bond may be, for example, a peptide bond, disulfide bond, thioester bond, amide bond, thioether bond, and the like. In one illustrative example, conjugates of monoclonal antibodies with drugs have been summarized by Morgan and Foon and by Uhr (1984). In another illustrative example where the conjugate contains a radionuclide cytostatic agent, U.S. Pat. No. 4,897,255, Fritzberg et al., is instructive of coupling methods that may be useful.

II. Dosages, Formulations and Routes of Administration of the Peptides, Polypeptides or Nucleic Acid Molecule (Agents) of the Invention The peptides or polypeptides of the invention are preferably administered at dosages of at least about 0.01 to about 100 mg/kg, more preferably about 0.1 to about 50 mg/kg, and even more preferably about 0.1 to about 30 mg/kg, of body weight, although other dosages may provide beneficial results. The amount administered will vary depending on various factors including, but not limited to, the agent chosen, the disease, whether prevention or treatment is to be achieved, and if the agent is modified for bioavailability and in vivo stability.

Administration of sense or antisense nucleic acid molecule may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al. (1995); Stevenson et al. (1995); Molling (1997); Donnelly et al. (1995); Yang et al. (1996); Abdallah et al. (1995)). Pharmaceutical formulations, dosages and routes of administration for nucleic acids are generally disclosed, for example, in Felgner et al., supra.

The amount of agent administered is selected to treat a particular indication. The agents of the invention are also amenable to chronic use for prophylactic purposes, preferably by systemic administration.

Administration of the agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms comprising the agents of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the agent with liquid carriers, solid matrices, semi-solid carriers, finely divided solid carriers or combinations thereof, and then, if necessary, introducing or shaping the product into the desired delivery system.

When the agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Formulations suitable for vaginal administration may be presented as pessaries, tampons, creams, gels, pastes, douches, lubricants, foams or sprays containing, in addition to the active ingredient, such carriers as are known in the art to be appropriate. Formulations suitable for rectal administration may be presented as suppositories.

Pharmaceutical formulations containing the agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The agents of the invention can also be formulated as elixirs or solutions for convenient oral administration or as solutions appropriate for parenteral administration, for instance by intramuscular, subcutaneous or intravenous routes.

The pharmaceutical formulations of the agents of the invention can also take the form of an aqueous or anhydrous solution or dispersion, or alternatively the form of an emulsion or suspension.

Thus, the agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The agents of the invention can be delivered via patches for transdermal administration. See U.S. Pat. No. 5,560,922 for examples of patches suitable for transdermal delivery of an agent. Patches for transdermal delivery can comprise a backing layer and a polymer matrix which has dispersed or dissolved therein an agent, along with one or more skin permeation enhancers. The backing layer can be made of any suitable material which is impermeable to the agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel gel), polyvinylidene chloride, poly(ethylene terephthalate), butyl rubber, epichlorohydrin rubbers, ethylenvinyl alcohol copolymers, ethylenevinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Agents released from a transdermal delivery system must be capable of penetrating each layer of skin. In order to increase the rate of permeation of an agent, a transdermal drug delivery system must be able in particular to increase the permeability of the outermost layer of skin, the stratum corneum, which provides the most resistance to the penetration of molecules. The fabrication of patches for transdermal delivery of agents is well known to the art.

For administration to the upper (nasal) or lower respiratory tract by inhalation, the agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the agent may be administered via nose drops, a liquid spray, such as via a plastic bottle atomizer or metered-dose inhaler. Typical of atomizers are the Mistometer (Wintrop) and the Medihaler (Riker).

The local delivery of the agents of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the agents may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms, e.g., via a coated condom. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of an agent of the invention present in a topical formulation will depend on various factors, but generally will be from 0.01% to 95% of the total weight of the formulation, and typically 0.1–25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

Any of the formulations described herein may include an amount of the metal which specifically binds to the metal binding domain of the molecule of the invention or the metal may be administered prior to or after administration of the molecule of the invention. Alternatively, an effective amount of the metal may be present in vivo. In one embodiment of the invention, a peptide or polypeptide which binds $Cu^{2+}$ is administered to a human in need thereof, for example, a human with $Cu^{2+}$ overload (Wilson's disease). The binding of $Cu^{2+}$ may result in a peptide or polypeptide which represses transcription, e.g., the peptide or polypeptide only binds DNA after $Cu^{2+}$ is bound or the binding of $Cu^{2+}$ results in a conformational change in the peptide or polypeptide that represses transcription of sequences adjacent to the sequence which is bound by the peptide or polypeptide.

The formulations and compositions described herein may also contain other ingredients such as antimicrobial agents, or preservatives. Furthermore, the active ingredients may also be used in combination with other agents, for example, oral contraceptives, bronchodilators, anti-viral agents, steroids and the like.

The invention will be further described by the following non-limiting example.

EXAMPLE

The remarkable similarity of the intermolecular interactions of many DNA binding proteins, despite little homology in their primary sequence, suggests that certain motifs are particularly well suited to complement the structure of B-form DNA (Brennan et al., 1989; Burley, 1994; Pabo et al., 1984; Patikoglou et al, 1997). The helix-turn-helix (HTH) motif is a well-known DNA binding motif which complements the shape of the DNA major groove. Homeodomains were first discovered in *Drosophila*, these small proteins bind DNA and regulate growth and development (Gehring et al., 1994; Komberg, 1993; Treisman et al., 1992). Homeodomains are transcription factors, either activators or repressors (e.g., Cro and λ repressors) which typically have about 60 residues in the homeodomain arranged as three helices, with the amino terminal arm contacting the minor groove (Burley, 1994; Patikoglou et al., 1997; Laughan, 1991). Homeodomains which comprise the HTH motif can specifically bind to DNA as a monomer or as a dimer which has enhanced affinity relative to a monomer (Freemont et al., 1991). The canonical HTH motif contains two orthogonal helices, spanned by a β-turn four residues in length (Patikoglou et al., 1997), although longer loops rather than β-turns may separate the two helices. The latter of the two HTH helices, the recognition helix, lies in the major groove of DNA allowing side chain contacts to be made to specific base sequences. However, the HTH geometry is not unique to transcription factors, but is in fact a common structural unit in proteins as diverse as Taq polymerase and Cyt c peroxidase.

In homeodomains, the HTH domain both interacts selectively with DNA and promotes translocation through cellular and nuclear membranes. Translocation is apparently an inherent property of these proteins, presumably dependent on the third helix of the HTH motif. This helix (α3) has in fact been shown to be a general membrane translocation vector for an array of hydrophilic cargoes, including non-native peptide sequences and DNA oligonucleotide fragments. The recognition helix of the homeodomain Antennapedia has even been dubbed "penetratin" for its remarkable ability to translocate to the nucleus via a receptor-independent internalization mechanism.

The similarity of the HTH and the Ca-binding EF-Hand structures was striking: these two motifs are variants of the α-α corner described by Efimov as part of his structural tree approach to protein classification (1984; 1986). Efimov concludes that this turn represents an inherently stable fold across a wide variety of non-homologous proteins. Thus, a design which maintains key α-helical regions, and interhelical hydrophobic and hydrophilic contacts, should result in a chimeric construct with a similar α-α corner structure.

Similar to the HTH in topology, but unrelated in function, is the ubiquitous Ca-binding motif, the EF-Hand. The EF-Hand, named for the orthogonal "thumb and forefinger" orientation between a pair of helices, contains a loop that incorporates the Ca(II) binding pocket (Celio et al., 1996). This Ca-binding loop comprises twelve residues, including six highly conserved, mostly acidic residues making side chain or backbone contacts to the metal. The motif commonly occurs in pairs in Ca(II) signaling and regulatory proteins, and in fact, isolated EF-Hand peptides have been found to form discrete dimers in solution ($Ca_2loop_2$) (Shaw et al., 1991; Wójcik et al., 1997; Clark et al., 1993). The subtle tuning of metal-specificity and cooperativity mediates the biological role of a given EF-Hand protein in signaling pathways. The dissociation constant for Ca(II) from an EF-Hand site is generally on the order of μM, though this varies with loop structure. EF-Hands sites exhibit a $10^6$ fold range in Ca(II) affinity, and up to a 1000-fold preferential specificity over Mg(II).

Lanthanide(III) ions have been successfully substituted into EF-Hands, with coordination geometries essentially identical to that of the native Ca(II) ion (Bruno et al., 1992; Falke et al., 1991; Coruh et al., 1994). Ln(III) ions are very similar in size to Ca(II) ions, and thus bind with higher affinity than Ca(II) due to their larger charge to size ratio. This greater charge density has been suggested to promote increased rigidity of structure in Ln-EF-Hands (Wójcik et al., 1997). Thus by selecting a Ln(III) ion and binding pocket, a sequence with high metal affinity, slow dissociation kinetics, and constrained geometry can be prepared. Further, lanthanide ions have been shown to enhance the rate of phosphate hydrolysis of enzymes by a factor of $10^7$, and provide excellent NMR, fluorescent, and luminescent spectral markers for studying structure and molecular interactions of biomolecules. Both metal-binding and hydrophobic interactions between helices promote the homeodomain's native tertiary structure, and thus its DNA binding function is also maintained.

Materials and Methods

Figure 1B:
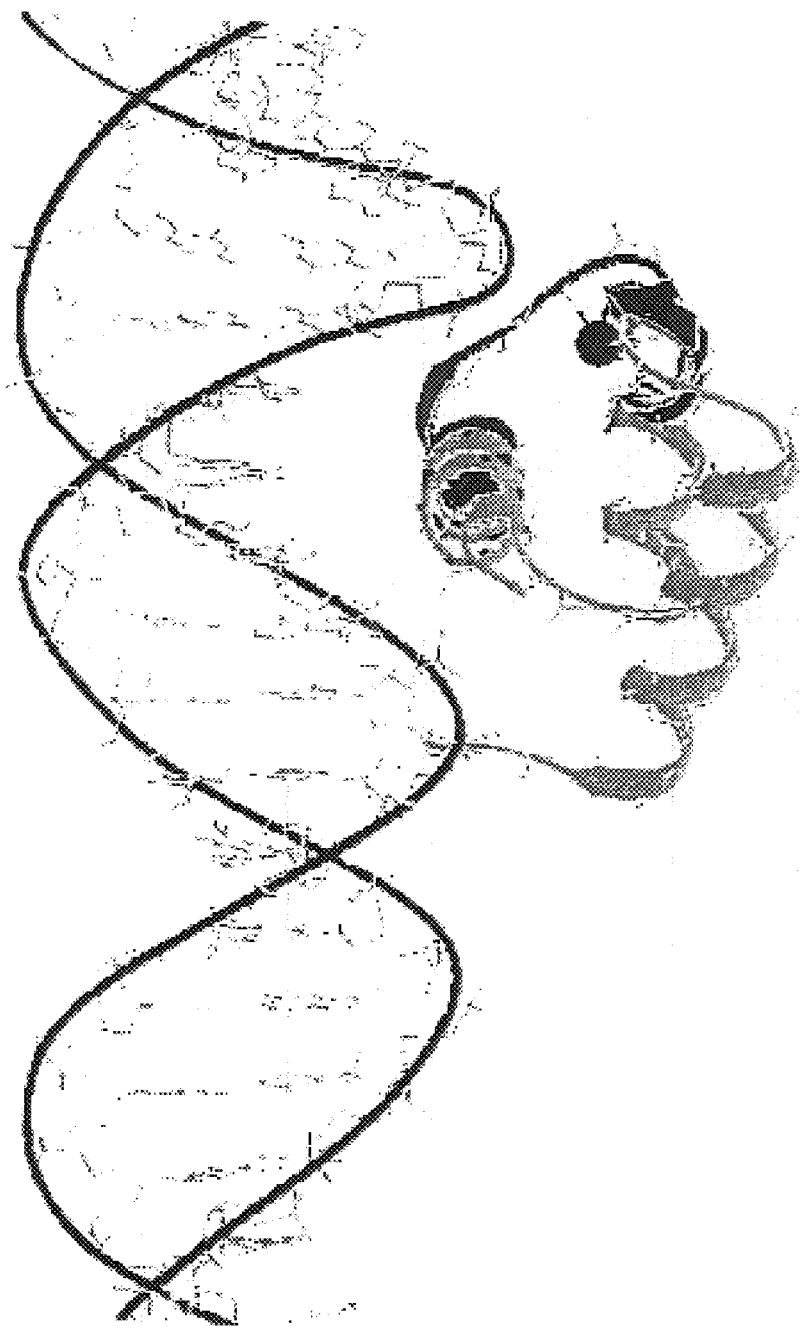
FIG. 1B. A side by side stereo view of double strand DNA (left; in blue) and a DNA and metal binding synthetic peptide (right; metal is shown as a blue sphere and synthetic peptide as a ribbon; in magenta and green).

Chimeric Design and Synthesis. The 33-residue peptides shown in FIG. 2 were based on overlays of engrailed and calmodulin crystal structures (FIG. 1B). Known protein crystal structures were oriented manually using the freeware program SwissPDBViewer (Guex et al., 1997) to align the fold of the homeodomain HTH motifs and Ca-binding protein EF-Hand motifs. Crystal coordinates were downloaded from the Protein Data Bank (PDB) for several EF-Hand proteins, such as calmodulin (1OSA) (Chattopadhyaya et al., 1992), parvalbumin (5PAL) (Roquet et al., 1992), and calcineurin (LTCO) (Kissinger et al., 1995). Coordinates for the homeodomain proteins engrailed (with and without co-crystallized DNA, 2HDD and 1ENH, respectively) (Clarke et al., 1994; Kissinger et al., 1990; Tucker-Kellogg et al., 1997) and antennapedia with DNA (9ANT) (Fraenkel et al., 1998) were obtained. The best fits (determined by inspection and RMS deviation of small helical sections) were used.

P3 is a consensus EF-Hand loop, P2 is a reverse EF-Hand loop, and P4a comprises α2 and α3 of engrailed, minus the last turn(s) of α2 and the β-turn, and contains calmodulin loop I (FIG. 2). The EF-Hand and calmodulin loop I motifs have two helices at approximate right angles to one another. P4a incorporates a greater fraction of the EF-Hand turn (single underline in FIG. 2) than does P3, as well as retaining the native salt bridges (Arg-Glu) and hydrophobic contacts (Phe-Phe) between the first turns of helix E and helix F, including an aromatic Tyr group ($Y_{13}$) in the loop, resulting in a shift in register of the Ca-binding loop to the N-terminal side.

The synthesis of peptides P2 and P3 was done by Dr. Suzanna Horvath of the Caltech Peptide Synthesis Facility, and P4a by Anaspec, Inc. The peptides were synthesized by Fmoc chemistry, cleaved from the resin, and HPLC purified to >95% purity. Concentrations of stock solutions were determined by Bradford assay (Bradford, 1976). $EuCl_3$ stock solutions were prepared by weight from $EuCl_3.(H_2O)_6$ (Aldrich, 99.99%), and adjusted to pH=6.0 with dilute NaOH.

Circular Dichroism Titrations. The titration of P2 and P3 peptides with Eu(III) and Ca(II) was followed by circular dichroism spectroscopy on an Aviv 60DS spectrophotometer at 25° C. Samples (50 μM peptide) were scanned from 260 to 200 nm (0.1 mm pathlength cell, 1.0 nm bandwidth, 0.5 nm resolution), in 10 mM Tris(hydroxymethyl)aminomethane buffer (Tris; pH=7.8). Eu(III) and Ca(II) were added as the chlorides. Aliquots of 10 mM stock metal solutions were added to a maximum of 10 equivalents.

The titration of free and metallated peptides with trifluorethanol (TFE) was followed by CD under similar conditions (1.0 cm pathlength cell). Aliquots of TFE were added to the buffered samples, which contained free peptide (25

μM P2 or P3), or 1:1 Eu-peptide (25 μM EuP2 or EuP3), in 5 mM Tris buffer (pH=7.8). Spectra were collected from 0 to 66% TFE.

Peptide helical content was calculated from molar ellipticity ($[\phi_{222}]$) at 222 nm, based on the following formula: $[\phi_{222}]=(100\times\phi_{222})/cnl$, where $\phi_{222}$ is millidegrees rotation at 222 nm, c is concentration of peptide in mM (corrected for dilution), n is the number of amino acid residues (33), and l is the pathlength in cm (Lehrman et al., 1990). Percent helicity was calculated assuming 100% $[\phi_{222}]=31,500$ deg·cm$^2$·dmol$^{-1}$ (Chen et al., 1972), and that only α-helical structure contributes to intensity at 222 nm.

$^1$H-NMR. The titration of P3 with Eu(III) was followed by $^1$H-NMR. Spectra were collected on a 400 or 600. MHZ Brüker Spectrospin spectrometer at 298 K with a 5 mm BBO probe. Each spectrum was recorded with a sweep width of 8013 Hz (32 acquisitions, 32768 total points). Samples of P3 (0.96 mM) were prepared in a solution of 50 mM imidazole-d$_4$ (98%; Cambridge Isotopes) and 50 mM NaCl, pH=7.5. Aliquots of EuCl$_3$ (25 mM stock, pH=6.0) were added directly to the NMR tube and the sample thoroughly mixed. Each sample was allowed to equilibrate for at least ten minutes prior to data collection.

The effect of concentration on EuP3 solution structure was followed by $^1$H-NMR (400 MHz). A sample of EuP3 (0.96 mM) was prepared in D$_2$O, 50 mM imidazole-d$_4$ buffer, 50 mM NaCl, pH7.5. Aliquots of buffer were added, lowering the concentration of EuP3 to 0.33 mM. Spectra were recorded as above.

DNA Gel Shift Assays. The affinity of EuP3, EuP2, and each free peptide for supercoiled plasmid DNA was examined by agarose gel electrophoresis. Plasmid (pBR322, New England Biolabs, Inc.) was incubated for 15 minutes at room temperature with increasing concentrations of each ligand (5–25 μM), prior to the addition of loading dye. Each lane contained 1 μg plasmid (50 μM base pairs) in 10 mM Tris buffer at pH 8.0. Agarose gels (1% agarose in 1×TAE buffer (Tris.Acetate.EDTA) were run for approximately 2 hours at 70–80 volts, then stained with a 1 μg/mL ethidium bromide solution overnight. The gels were visualized under UV light and photographed with Polaroid 3000 ISO 667 film. The photographs were scanned, and DNA concentrations quantified with ImageQuant software (Molecular Dynamics). Control lanes containing only plasmid, buffer, and dye were treated in the same manner as other samples. No precipitation was observed in the samples. Similar results were found with pUC19 plasmid.

Metal binding and solution structure. The binding affinity of P3 for Eu(III) was characterized by isothermal titration microcalorimetry. The dissociation constant for EuP3 was found to be 10±4 μM, from which the amount of bound and free Eu(III) in solution was calculated (Table 1). Though there is only one binding site per peptide, the binding behavior was not a simple two species process. EuP3 also dimerizes at higher concentrations $K_{dim} \geq 80$ μM. However, the second metal site in the dimer has low affinity ($K_d$>1 mM), so free Eu(III), EuP3 monomer, and a singly occupied dimer (EuP3$_2$), are the species present at concentrations below 100 μM.

TABLE 1

Rates of BNPP$^+$ cleavage as a function of Eu-peptide at 37° C.

| Concentration (μM Eu/μM P3) | [EU$_{free}$] (calc; μM) | [EuP3] (calc; μM) | [EuP3$_2$] (calc; μM) | Rates (K$_{(obs)}$) (s$^{-1}$ × 10$^7$) |
|---|---|---|---|---|
| 10/10$^a$ | 6.2 | 3.7 | 0.3 | 6.0 |
| 25/25$^a$ | 11.6 | 11.8 | 1.8 | 7.3 |
| 25/50$^a$ | 5.2 | 15.3 | 5.3 | 20.6 |

TABLE 1-continued

Rates of BNPP$^+$ cleavage as a function of Eu-peptide at 37° C.

| | | | | |
|---|---|---|---|---|
| 50/50$^b$ | 18 | 27 | 5 | 17.5 ± 4 |
| 50/100$^b$ | 8 | 28 | 14 | 11.5 ± 4 |
| 10/0$^b$ | 10 | — | — | 5.2 ± 0.6 |
| 12/0$^b$ | 12 | — | — | 5.7 ± 0.3 |
| 20/0$^b$ | 20 | — | — | 19 ± 3 |

| Eu/P4a | [EU$_{free}$] | [EuP4a] | [EuP4a$_2$] | |
|---|---|---|---|---|
| 10/10$^a$ | 4 | 6 | | 11.3 |
| 25/25$^a$ | 7 | 18 | | 56.3 |
| 25/50$^a$ | 2 | 22 | 1 | 62.0 |
| 50/50$^a$ | 11 | 38 | 1 | 149.5 |
| 50/100$^a$ | 2 | 44 | 4 | 212.0 |

| EuCl$_2$ | [EU$_{free}$] | — | — | |
|---|---|---|---|---|
| 10/0$^a$ | 10 | — | — | 1.4 |
| 15/0$^a$ | 15 | — | — | 2.0 |
| 20/0$^a$ | 20 | — | — | 2.7 |

| Eu/EuP5L | [Eu$_{free}$] | [EuP5L] | [EuP5L$_2$] | |
|---|---|---|---|---|
| 10/10$^b$ | 7.2 | 2.8 | 0 | 19.5 ± 4 |
| 50/50$^b$ | 23 | 22 | 5 | 30.8 ± 3 |

$^+$BNPP concentration = 500 μM, pH = 7.7, 10 mM Tris buffer$^a$ or 5 mM Tris buffer$^b$.
$^a$Calculated [EuP3], [EuP3$_2$], and [Eu$_{free}$] values are based on the measured dissociation constants for EuP3 (K$_d$ = 10 μM; K$_{dim}$ ≥ 80 μM) and EuP4a (K$_1$ = 3 μM; K$_{dim}$ ≥ 300 μM).
$^b$Calculated [EuP3], [EuP3$_2$] and [Eu$_{free}$] values are based on the measured dissociation constant for EuP3 (K$_d$ = 10 μM). Calculated [EuP5L] and [Eu$_{free}$] values are based on an estimate of K$_d$ = 20 μM. Error limits; K$_{obs}$ = ±2%.

Results

Chimeric Design. Overlays of the HTH and EF-Hand motifs showed remarkable similarity in overall shape, and served as a basis for chimeric design (FIG. 1). The crystal structure coordinates of several homeodomain (engrailed, with and without co-crystallized DNA, Clark et al., 1994 and Tucker-Kellogg et al., 1995; and Antennapedia without, Frankel et al., 1998) and Ca-binding proteins (calmodulin, Chattopadhyaya et al., 1992; parvalbumin, Roquet et al., 1992; and calcineurin, Kissinger et al., 1995) were obtained from the Protein Data Bank, and overlayed using the protein visualization program SwissPDBViewer. The EF-Hand loop region was aligned such that the helix axes of each motif were colinear. These motifs consist of two helices at approximate right angles to one another, and as such, can be overlaid either parallel or antiparallel. The parallel orientation is required for correct sequence design. Generally, overlays showed similar helix orientations in 3-dimensions, though some deviation in α-α angle between various HTH or EF-Hand motifs resulted in a range of fits. The best fits (determined by inspection and RMS deviation of small helical sections) were used for further peptide sequence design. For example, the HTH of engrailed homeodomain (residues 27–56, 1ENH) was found to be particularly complementary in α-α angle to the third EF-Hand loop of calmodulin (residues 93–104, 1OSA) and to the second EF-Hand loop of parvalbumin (residues 79–108, 5PAL, FIG. 1).

In order to maintain the same 3D orientation of α2 and α3, the last turn of α2 needed to be omitted when including the EF-loop. If just the four residues of the turn from the HTH were replaced, then α2 was displaced in space one turn (about 4 Å) in the N-terminal direction, destroying potential α2-α3 hydrophobic stabilization at the turn. Based on these observations, a peptide was designed and synthesized (FIG. 2). P3 comprises α2 and α3 of engrailed ($T_{27}$–$L_{34}$ and $E_{42}$–$K_{57}$) and the twelve-residue consensus EF-Hand Ca-binding loop (Falke et al., 1994). Three additional residue substitutions were made ($X_{(n)}$ denotes numbering scheme). The substitution of $A_{43} \rightarrow R_{(19)}$, the residue which occurs in the related Antennapedia homeodomain sequence, incorporated an additional basic residue to strengthen electrostatic interactions with DNA. A second modification ($Q_{44} \rightarrow E_{(20)}$) maintained the conserved Glu at the twelfth position of the EF-Hand loop, and the $W_{48} \rightarrow H_{(24)}$ substitution was incorporated for ease of synthesis by Fmoc chemistry. Based on the parent crystal structures, sites of Ca(II) or Ln(III) binding are indicated by an x P3.

P4 comprises α2 and α3 of Engrailed, minus the last turn(s) of α2 and the β-turn, and contains calmodulin loop I, P5 comprises α2 and α3 of Antennapedia and calmodulin loop III. The abbreviated 20-mer peptide P5L comprises the loop region of P5 ($F_6 \rightarrow F_{25}$). P4, P4a and P5 incorporate a greater fraction of the EF-Hand turn which likely improves the fold, as the native salt bridges (Arg-Glu) and hydrophobic contacts (Phe-Phe or Phe-Val for P4a) between the first turns of helix E and helix F are retained. CM1 is a loop modified Engrailed peptide.

A control peptide (P2) was also synthesized. This peptide included the same features as P3, but with the 12-residue consensus Ca-binding loop sequence reversed. P2 was predicted not to bind or fold effectively, allowing the comparison of positive and negative de novo design within synthetic peptides of similar size and construction. The helical regions of engrailed (α2 and α3) were incorporated as in P3, but with a difference in register, based in part on an anti-parallel structural alignment. No substitution for $W_{48}$ was made in P2 ($W_{(26)}$).

Figure 3A:
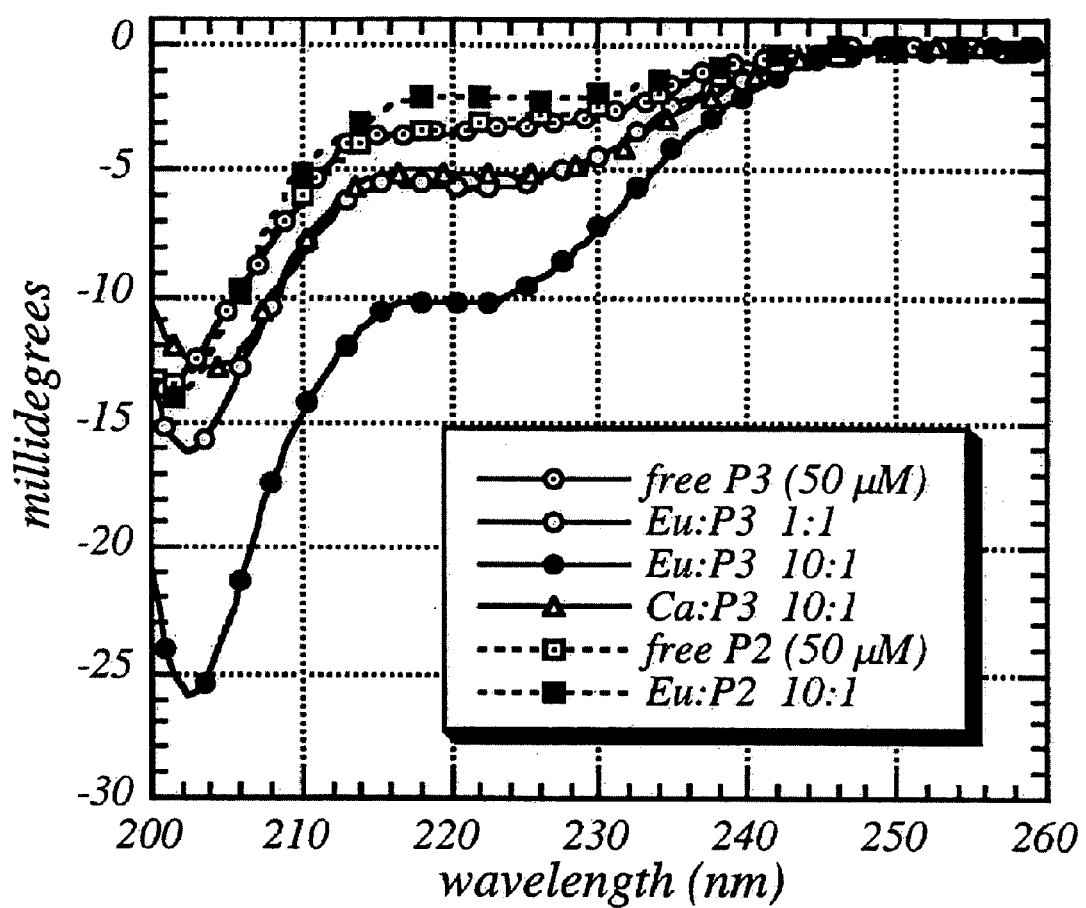
FIG. 3A. CD spectra of P2 and P3 peptides with and without Eu(III) and Ca(II) (10 mM Tris buffer, pH=7.8, 25° C., 0.1 mm cell).
Figure 3B:
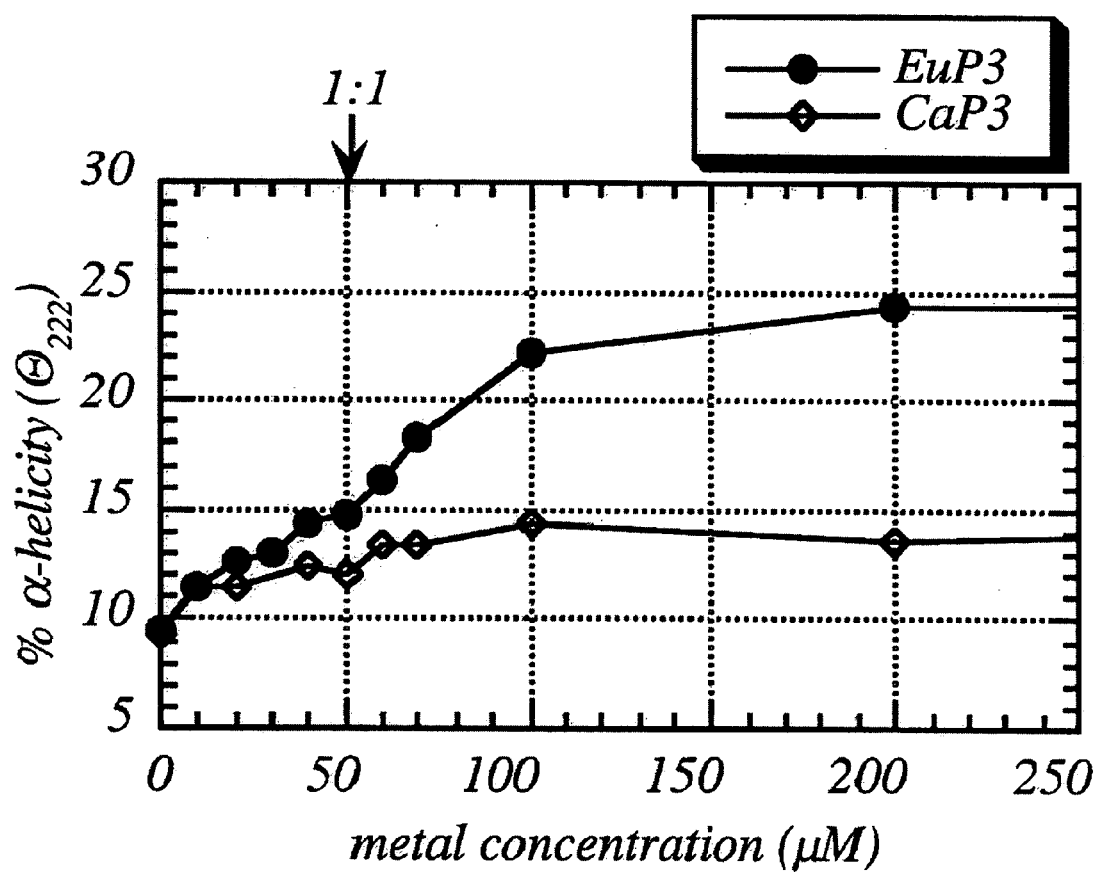
FIG. 3B. Graph of $\alpha$-helicity versus metal concentration for EuP3 and CaP3.

Circular Dichroism Titrations. To establish that these peptides have structure in solution, and whether this structure is influenced by metal binding, the induced helicity of the peptides was measured as a function of added metal. The CD spectra of free P2 and P3, and each peptide with La(III), Eu(III), and Ca(II) was investigated in $Na_2HPO_4$ and Tris.HCl buffers (25–50 μM peptide; FIG. 3). The spectra had minima at 222 nm, indicating some amount of α-helical structure (Saxena et al., 1971). For the control peptide (P2; 50 μM), the addition of metal does not appreciably increase secondary structure. The metal-saturated P3 spectrum is nearly identical for Eu(III) and La(III), but was not achieved at 100-fold excess Ca(II) (25 μM peptide). This is consistent with the expected lower binding affinity of the divalent ion. No further changes are seen in the 100-fold excess La(III) and Eu(III) spectra.

The secondary structure of P3 as a function of metal was followed by CD, calculating the % α-helicity from the molar ellipticity at 222 nm (100% helical=−31,500 deg $cm^2$ $dmol^{-1}$). With the addition of Eu(III) to P3, the helicity increases from 9 to 25%, showing enhanced structure correlated to metal-coordination. This increase in structure with added metal describes a curve which has an inflection point at approximately 1:1 Eu:P3, then continues to a 25% helical metal-saturated form. Metal binding affinity ($K_1$) can be estimated from the initial portion of the curve (0–50 μM) to be $K_1$ about 10 to 20 μM, in good agreement with the calorimetry data. A second structural change, correlating to the discrete back-to-back dimerization which has been well characterized for similar EF-Hand peptides systems occurs at $K_{dim}$ about 80 μM (Shaw et al., 1991; Wójcik et al., 1997; Clarke et al., 1993; Shaw et al., 1990; Maurer et al., 1995). The addition of Ca(II) causes the same initial structural change (increasing to 14% helical content), but no further change in the metal saturated form. This may reflect weaker, less rigid binding by the $2^+$ versus $3^+$ ions, as described by Clark with similar isolated EF-Hand loops (Clark et al., 1993), or less tendency to dimerize with Ca(II) ions, as described by Wójcik et al. (1997).

Induced secondary structure. The nucleation of structure by metals can be indirectly studied by the observation of CD spectral changes with added trifluorethanol (TFE), an agent known to enhance α-helicity and β-hairpins in proteins by favoring internal protein hydrogen bonds over those of the solvent (Lu et al., 1997, Cammers-Goodwin et al., 1996; Starrs et al., 1992). TFE serves to stabilize local minima in structure. Thus, a helix induction curve (molar ellipticity versus % TFE) that has plateaus indicates something more than random helix formation, e.g., a preferred 2° or 3° structure within the protein, and can therefore illuminate differences in the inherent structural stability of various species.

Figure 4:
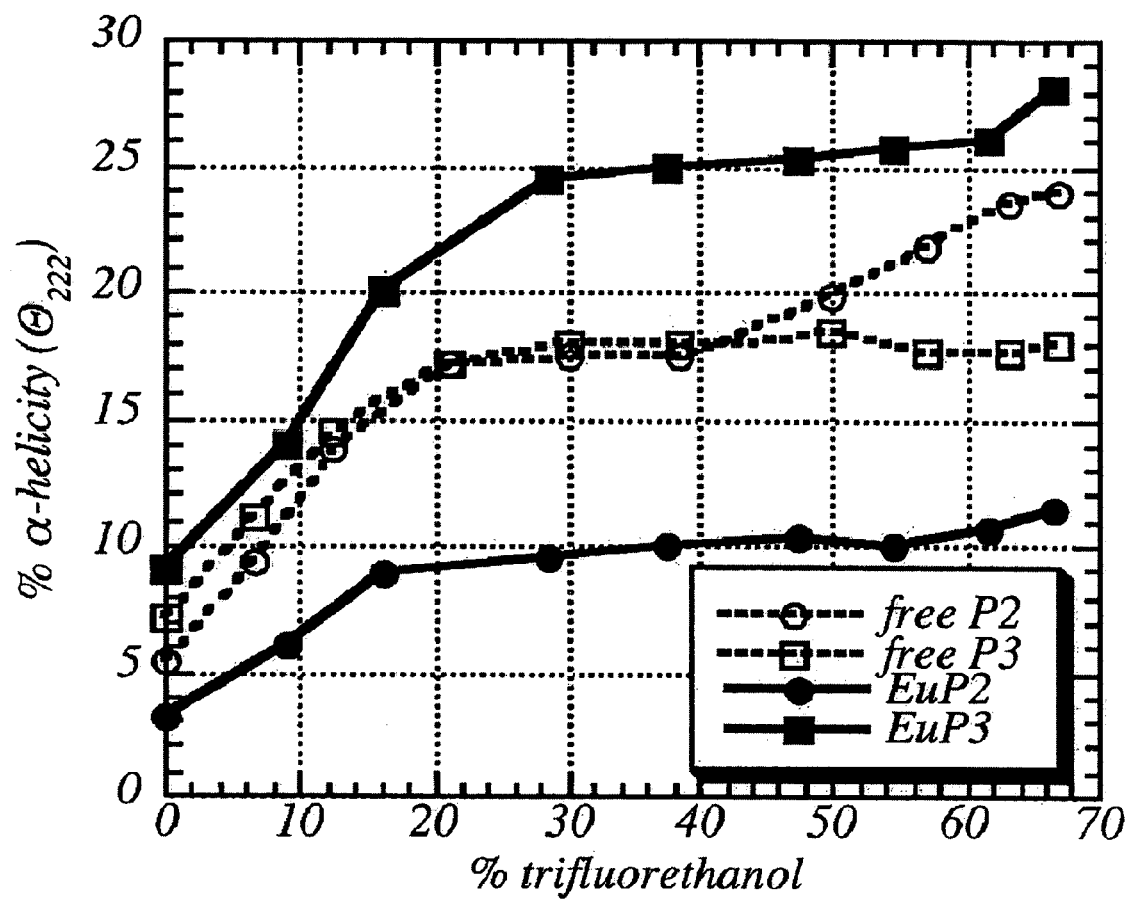
FIG. 4. TFE helix induction curve of P2, P3, EuP2, and EuP3 (25 µM each, 10 mM Tris buffer, pH=7.8, 25° C.). The $\alpha$-helicity calculated from the molar ellipticity at 222 nm varies as a function of increasing trifluoroethanol solvent.

The helix induction curve for free P2 and P3 peptides, and each with Eu(III) is shown in FIG. 4 (25 μM Eu:peptide, 5 mM Tris buffer, pH=7.8). All have plateaus in the curve, showing that they have inherent structural tendencies. The peptides alone initially have very similar behavior, likely because of the similarity in the α2, α3 regions derived from the homeodomain, which have a propensity to form helices. However, the Ca-binding loop of P3 resists further α-helix formation at higher TFE concentrations, since the loop has a preference for β-turn structure. P2, in contrast, has no defined loop, so a further linear increase in helicity is seen at greater than 40% TFE.

Upon the addition of metals, very different behavior is seen for the designed and control peptides. For P2, added Eu(III) decreases helicity (even at 0% TFE), inhibiting the tendency of the peptide to form helices. For P3, however, added Eu(III) significantly increases the α-helicity, reaching a plateau at an α-helical content similar to the metal saturated spectrum in water (FIG. 3, at 50 μM peptide). As was the case for free P3, EuP3 resists further structural changes until a much higher percent TFE. The helix induction curve suggests that EuP3 has a tendency to adopt a defined structure with significant helical content, consistent with a native-like fold.

Figure 5A:
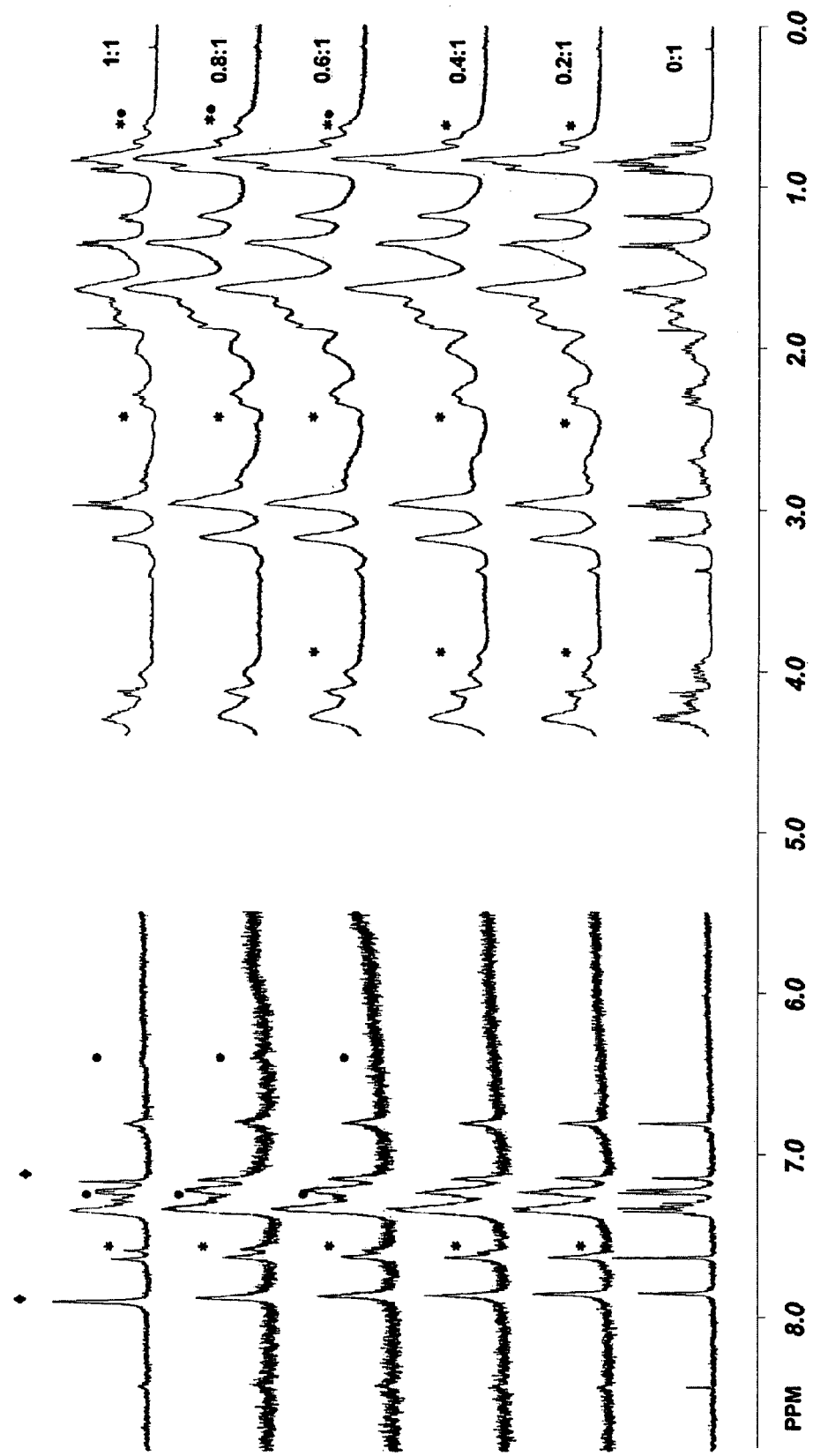
FIGS. 5A–B. Titration of P3 with $EuCl_3$ followed by $^1$H-NMR (400 or 600 MHZ, panels A and B, respectively). A) A 1.0 mM sample of P3 was prepared in $D_2O$, 50 mM imidazole-$d_4$ buffer, 50 mM NaCl, pH=7.5. The residual HOD peak is omitted for clarity, and the aromatic region is presented at x intensity. In panel A, imidazole buffer resonances are indicated with ♦; and selected EuP3 peaks are indicated: those occurring between 0 and 0.5 equivalents titrated are marked with *, and those appearing between 0.5 and 1 equivalents titrated are marked with •.
Figure 5B:
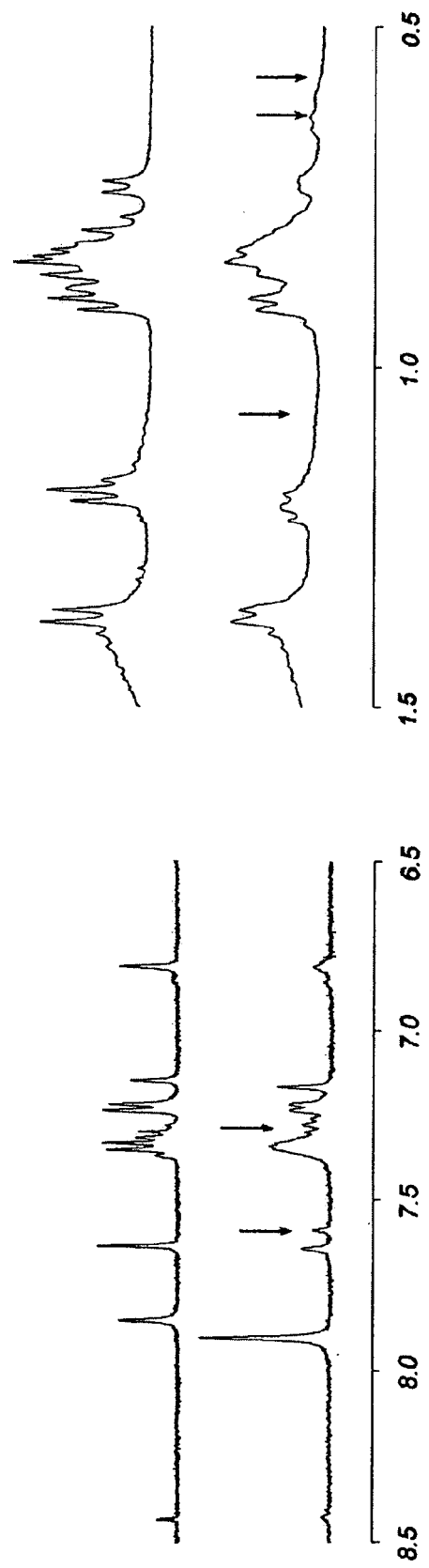

$^1$H-NMR. The 400 and 600 MHZ $^1$H-NMR spectrum of P3 in $D_2O$ in the presence and absence of equimolar Eu(III) shows changes in solution structure upon binding (FIGS. 5A–B). The peaks in the spectrum of the apo-peptide are sharp and have little signal dispersion. The addition of $EuCl_3$ results in new resonances due to metal-bound peptide in slow-exchange with free P3. The new resonances are somewhat broadened relative to free P3 signals, but still well resolved. Appreciable mixing time between additions (up to 30 minutes) is required for full equilibration.

Figure 6:
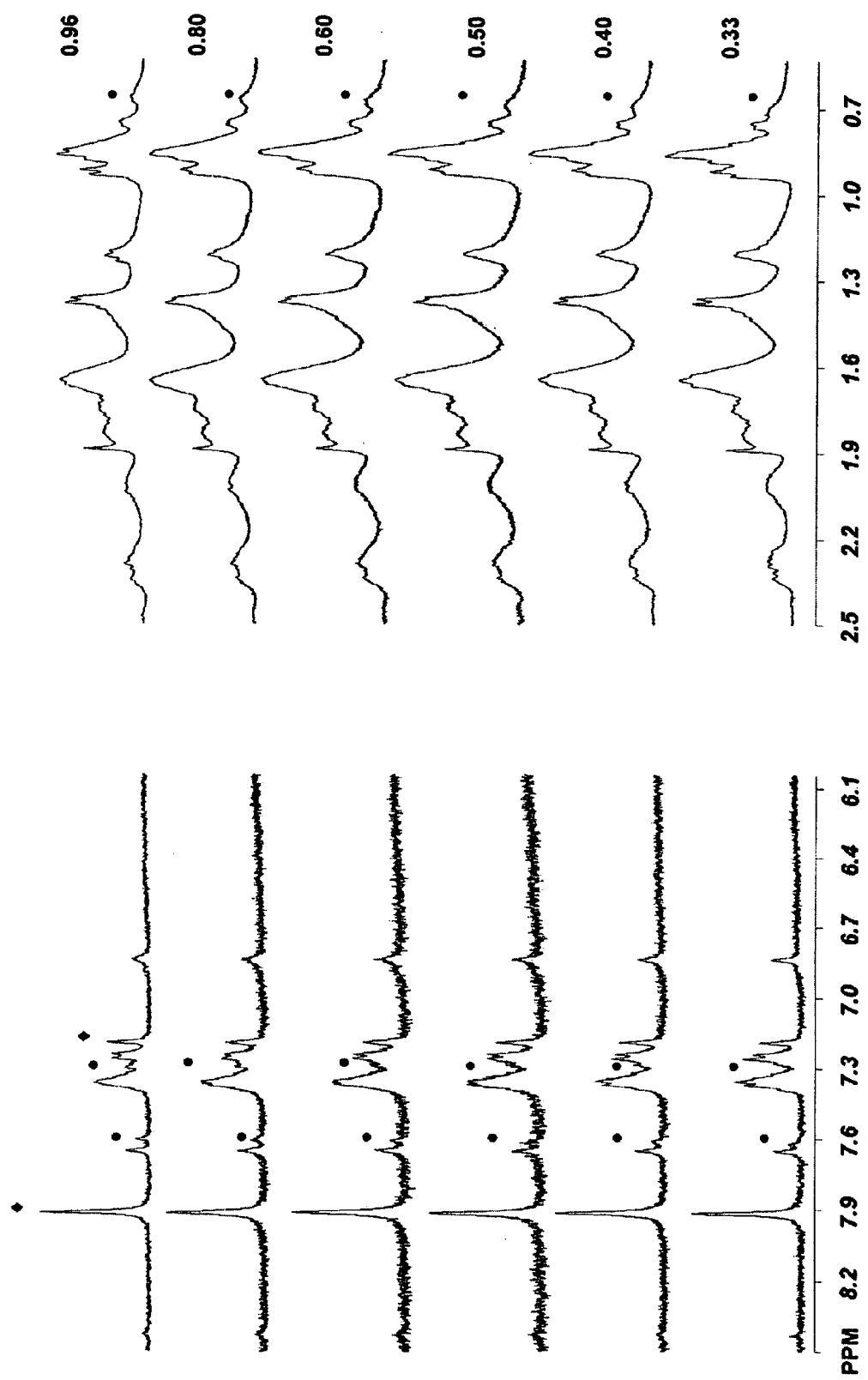
FIG. 6. Dilution study of EuP3 followed by $^1$H-NMR (400 MHZ; expanded regions shown). A sample of EuP3 (0.96 mM ) was prepared in $D_2O$, 50 mM imidazole-$d_4$ buffer, 50 mM NaCl, pH=7.5. Aliquots of buffer were added, lowering the concentration of EuP3 to 0.33 mM. Selected EuP3 peaks which disappear with dilution are indicated with •. Imidazole buffer resonances are indicated with ♦. The residual HOD peak is omitted for clarity, and the aromatic region is presented at x intensity.

Several peaks characteristic of folded EF-Hands appear as a function of metal (Shaw et al., 1991; Shaw et al., 1990; Akke et al., 1991; Chen et al., 1998; Shaw et al., 1996). Particularly diagnostic are the upfield shifts of Ile γ $CH_3$ protons, to 0.6–0.7 ppm. The changes in the spectrum due to Eu-bound peptide (peaks marked with *, in FIG. 5A) predominantly occur within the first 0.5 equivalents of metal added, supporting the conclusion that the peptides dimerize to a singly-occupied $EuP3_2$ structure. This titration behavior is also observed with native EF-Hand peptides (Shaw et al., 1991; Shaw et al., 1990; Akke et al., 1991; Chen et al., 1998; Shaw et al., 1996), for which one metal ion is sufficient to nucleate the fold of two EF-Hand peptides. However, at the relatively high concentration of the NMR experiment (0.96 mM), a second lower affinity site can also be populated. Thus the spectrum continues to change with the titration of the second half-equivalent of metal, to give the fully occupied dimer form. As this solution is diluted (FIG. 6), the low affinity site becomes unpopulated, and the spectrum approaches that of the singly-occupied dimer recorded with 0.5 equivalents of metal.

Both the binding affinity estimates from CD and microcalorimetry, and the stoichiometry of the EuP3 NMR titration support the conclusion that the spectral changes are due to dimerization, and not simple metal binding. The synthetic peptides thus mimic EF-Hand behavior, dimerizing first to a singly-occupied $Eu(P3)_2$ structure analogous to the native EF-Hand fold, then to the fully metallated dimer, $Eu_2(P3)_2$.

DNA Affinity. The interaction of these peptides with DNA was investigated by agarose gel electrophoresis assays of supercoiled plasmids. The interaction of ligand with supercoiled plasmid (type I) can be observed if run under conditions where the DNA-ligand interactions are not disturbed during electrophoresis. Supercoiled pBR322 was chosen as a standard plasmid, and was incubated for 15 minutes with $EuCl_3$, EuP3, EuP2, or free peptide prior to electrophoresis. This small, 4,361 bp plasmid contains three 5'-TAATT-3' sequences, and eight 5'TAAT5' sequences, partial target sequences for engrailed homeodomain. In the absence of 0.1 M EDTA (normally added prior to electrophoresis to quench hydrolytic cleavage assays) and with short incubation times to minimize metal-catalyzed cleavage, a gel shift can be observed. This gel shift and disappearance of type I plasmid occurs as a function of EuP3, but not $EuCl_3$ alone. Additionally, there is no shift due to EuP2, suggesting that the sequence, and thus structure, of the peptide is important for this effect. P3 has two additional positive residues relative to P2, which may enhance DNA interactions, and in fact, a gel shift is also observed for free P3, though at slightly higher concentrations.

Figure 7:
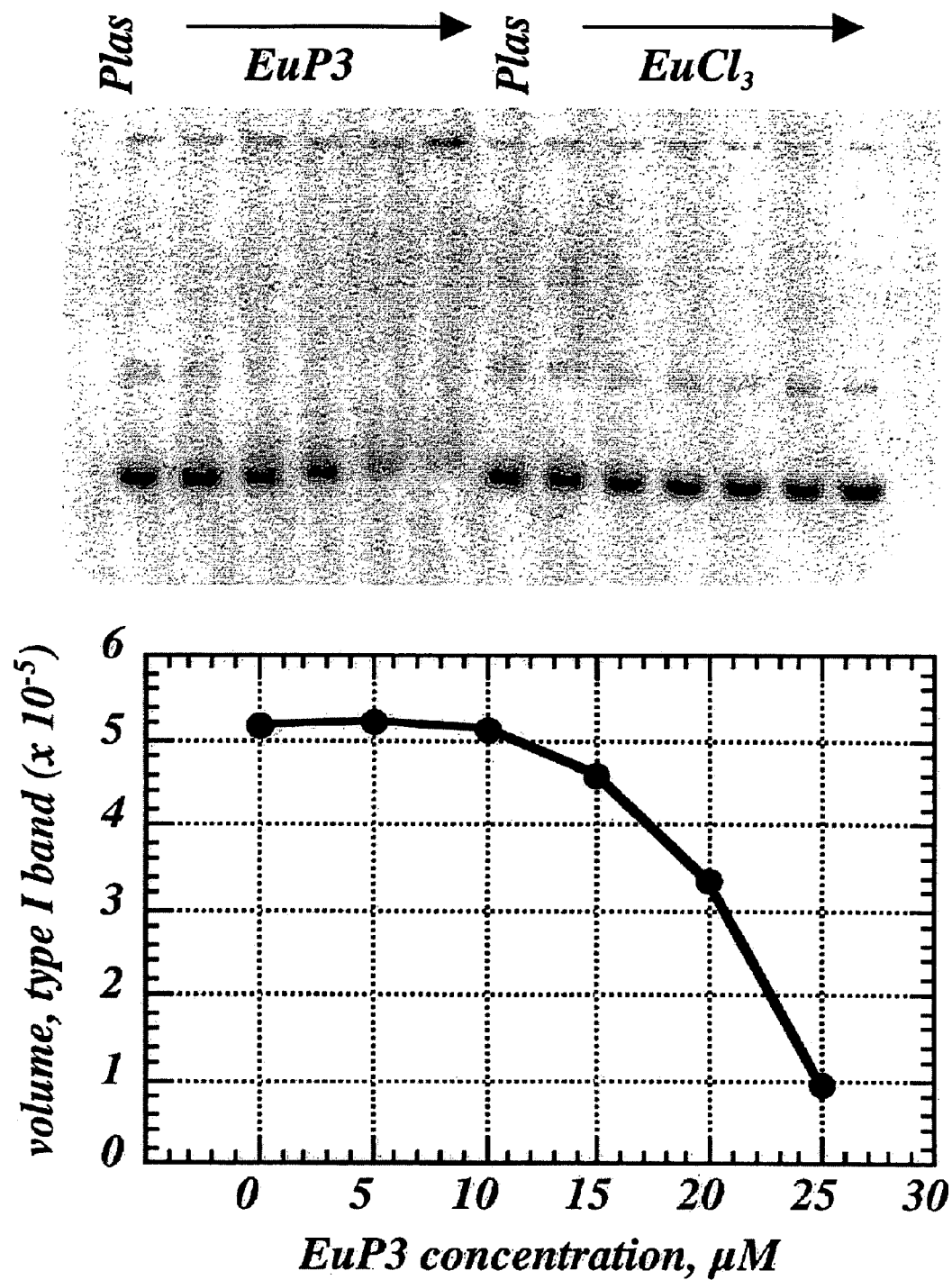
FIG. 7. The top panel is a representative gel showing the disappearance of type I band (supercoiled pBR322 plasmid) as a function of increasing EuP3 (5–25 µM). This gel shift is not seen with free metal over the same concentration range (right lanes), or with the control peptide, P2. An attenuated shift is observed for free P3. The lower panel is a graph showing quantified volumes of type I band (arbitrary volume units) as a function of EuP3 concentration. Data are an average of three gel shift assays.

From quantified concentration-dependent gel shift data, an estimate of the binding affinity of EuP3 can be made. Gels with increasing Eu-peptide concentrations (5 to 25 µM in each set) were quantified (ImageQuant; Molecular Simulations), and average band volumes were plotted versus concentration. The disappearance of type I band as a function of EuP3 is shown in FIG. 7, along with a representative gel. Each graphed point represents data averaged from three gel experiments. These data indicate that the EuP3 binds DNA in the 20 µM range. No such shift is observed for EuP2.

Hydrolytic Phosphate Cleavage. Because the EF-Hand is physiologically strictly a structural motif, an isolated Ca-binding loop's ability to affect hydrolytic cleavage was addressed. The hydrolysis of bis-nitrophenylphosphate (BNPP) was followed spectrophotometrically under turnover conditions. The absorbance increase at 400 nm due to liberated 4-nitrophenolate was observed over the initial 10–14 hours of the reaction ($\leq 10\%$ BNPP converted). No measurable hydrolysis of BNPP was observed in the absence of metal. Plots of absorbance vs. time were converted to concentration units ($\epsilon=18,500$ $M^{-1}$ $cm^{-1}$) to give first order rate constants (Sardesai et al., 1994).

The synthetic metallopeptide catalyzes BNPP hydrolysis with rate constants on the order of $k=10^{-6}$ $sec^{-1}$ (Table 1), comparable to other Ln catalysts (Morrow, 1994; Chappel et al., 1998). This represents a rate increase of approximately $10^6$ over uncatalyzed reactions, showing that the metal in the Ca-binding motif is indeed accessible enough to be hydrolytically active (at 37° C., pH=7, BNPP is hydrolyzed with an estimated rate of $6 \times 10^{-1}$) (Chin et al., 1989). While EuP3 cleavage may not be as fast as free Eu(III) catalysis, cataly-sis by EuP5L apparently is. This may be due to a more flexible and open coordination environment in this abbreviated peptide. Notably, the concentrations of free Eu(III) calculated from the measured dissociation constants are not alone sufficient to explain the cutting rates.

Figure 8:
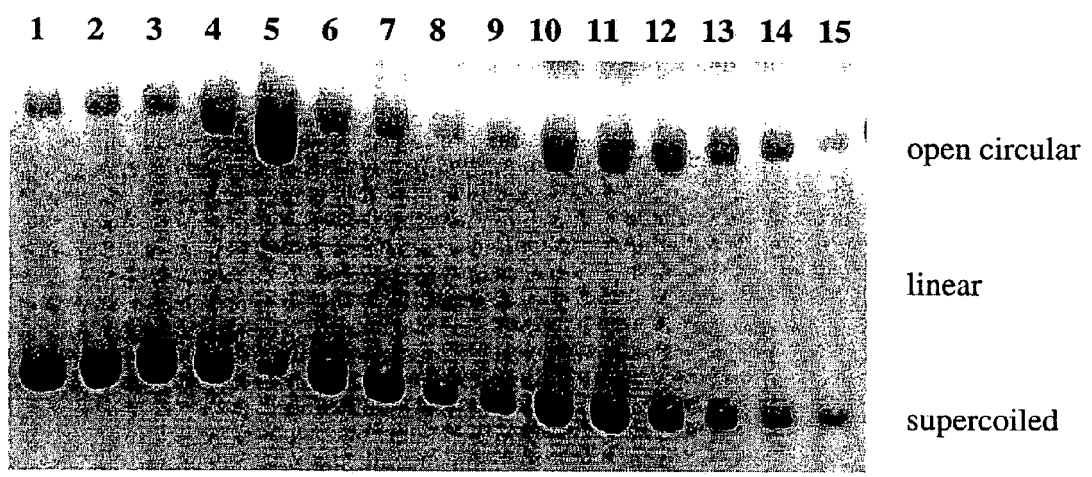
FIG. 8. Agarose gel electrophoresis showing the cleavage of pUC19 plasmid DNA by EuP3. Samples containing 1 µg plasmid (about 60 µM b.p.) in 10 mM Tris buffer, pH=7.0, were incubated for 48 hours at 37° C. Reactions were quenched by the addition of 0.5 M EDTA to a final concentration of 0.1 M, followed by addition of 100 mM KCl. The reaction mixtures were then treated with Amberlyst cation exchange resin prior to electrophoresis. Lane 1: pUC19 DNA control; lanes 2–5: DNA plus increasing concentrations of EuC13 (20, 30, 50 and 100 µM); lanes 6–9: DNA plus increasing concentrations of free P3 (20, 30, 50 and 100 µM); lanes 10–15: DNA plus increasing concentrations of 1:1 Eu:P3 (10, 20, 30, 40, 50 and 100 µM). At the higher concentrations (lanes 13–15), significant affinity for DNA causes a decrease in total DNA intesity, likely due to aggregation causing insolubility.
Figure 9:
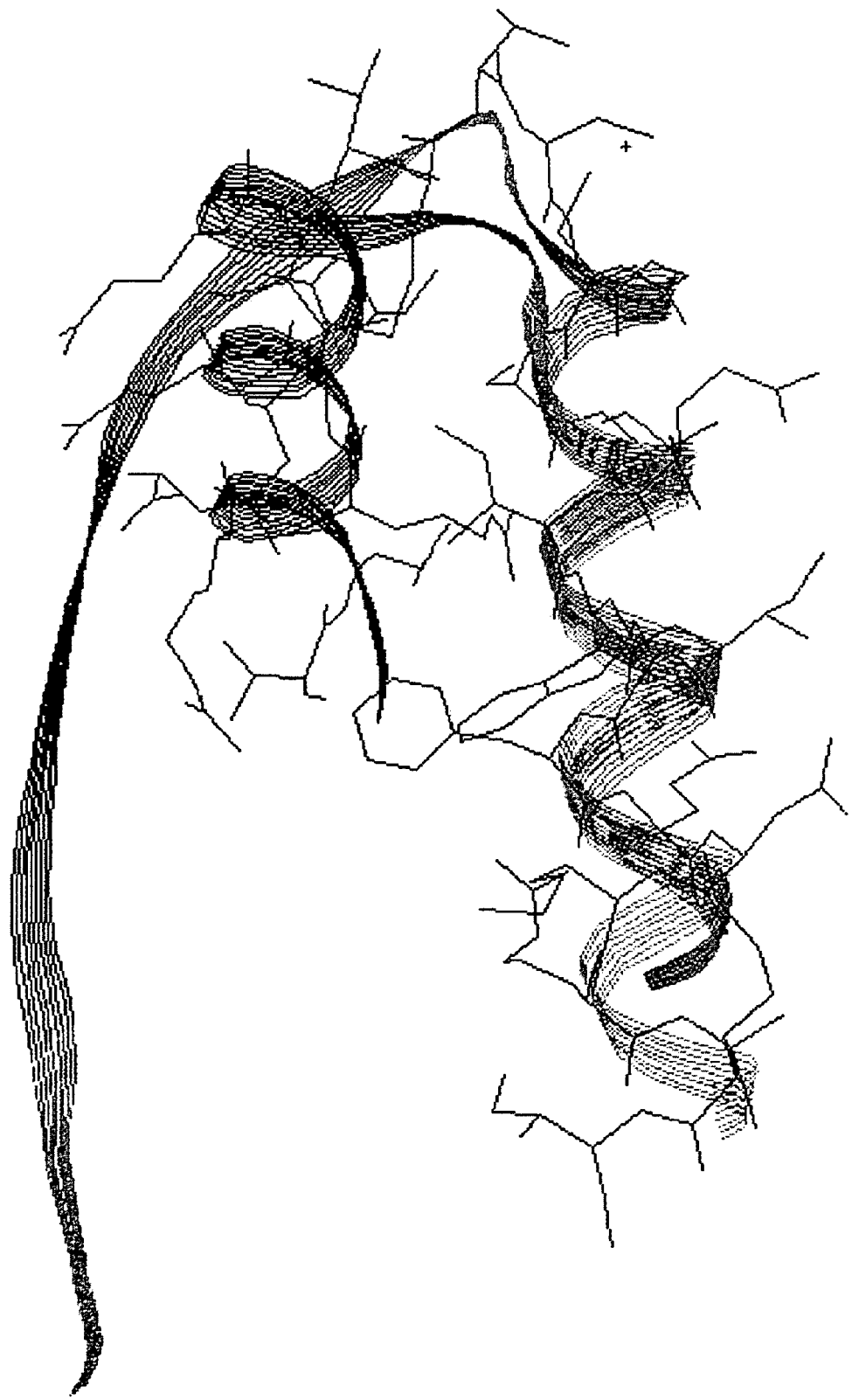
FIG. 9. Stereoview of the overlay of the helix-turn-helix of engrailed and the helix-loop-strand of the copper binding domain of Atx1.

Moreover, as shown in FIG. 8, EuP3 catalyzes the cleavage of supercoiled, double-stranded DNA as well as model compounds. The conversion of supercoiled plasmid (type I) to open circular (type II), linear (type III), or smaller fragments was monitored by agarose gel electrophoresis. Because the synthetic peptides bind strongly to DNA, thus preventing the observation of products, the peptides were chelated prior to electrophoresis (Falke et al., 1994). At the point each reaction was quenched (0.1 M EDTA), a suspension of neutral, washed, cation resin (Amberlyst, 10–20 µL) was incubated with each sample for 30 minutes, spun down, and the supernatent loaded into wells. After 24 hours of reaction (incubated at 37° C.), the concentration-dependent formation of open circular plasmid was observed (FIG. 8). Higher concentrations of EuP3 are less effective (slower), in keeping with the model BNPP system. Also of note is that 25 µM EuP3 in the presence of 225 µM excess metal has a similar effect to 25 µM EuP3 alone, suggesting that peptide bound to DNA blocks indiscriminate Eu cleavage. Over a 10–300 µM EuP3 gradient, nicking occurred from 10–150 µM, with the greatest amount of cleavage at 30 µM EuP3. EuP3 activity falls off with increasing concentration likely due to dimerization. Surprisingly, EuP4a activity does not.

Interestingly, the observed phosphate and DNA cleavage rates show an inverse dependence on catalyst concentration, correlating to the dimerization of two P3 or EuP3 moieties. This suggests that while a monomeric EF-Hand is catalytically active, the metal ions in supersecondary native-like dimer structures are not accessible for catalysis. Thus, HTH/EF-hand chimeras bind metals, have metal-dependent solution structure, and interact with and cleave DNA.

Discussion

It is of great interest to generate artificial repressors to target sequences of choice, not only for the biochemical utility of such agents, but for the pharmaceutical impact of drugs which could target a single promoter region on the genome. Toward this end, an isolated peptide motif which binds Eu(III) and Ca(II), has enhanced solution structure as a function of metal, and binds DNA, in analogy to its unrelated parent domains was prepared. The chimeric approach to the design of selective DNA binding units employs the same highly specific, yet flexible protein-DNA interactions which cells themselves use to regulate their growth.

Based on their metal-binding and solution behavior, the synthetic peptides can be classified as true EF-Hand derivatives. Isolated EF-Hand peptides have been shown to have significant affinity for lanthanides, commonly ranging from $K_d=10$ to 50 µM depending on loop sequence (Dadlez et al., 1991; Goch, 1999; Siedlecka et al., 1999). This Ln(III) affinity is only slightly lower than that of typical EF-Hands in the context of proteins ($K_d=6$ nM to 3 µM) (Bruno et al., 1992; Burroughs et al., 1994; Drake et al., 1996), suggesting that this motif is inherently well-organized into an Efimov-type α-α turn. The CD titration showed that the designed peptide P3 folds as Eu(III) is incorporated, with $K_d \leq 20$ µM, similar to native EF-Hand peptides. The control peptide P2, however, does not fold in the presence of Eu(III). Instead the helical content remains unchanged or even decreases (depending on peptide concentration) as a function of added metal. This is expected for random metal binding to various acidic sidechains; rather than nucleating helix formation by bringing together favorable hydrophobic and electrostatic residues as a single metal-binding site is organized, random binding to multiple weak sites would disfavor defined secondary structure.

The CD results for Eu(III) binding to P3 show a further equilibrium event which we assign to dimerization; both the metal-binding ($K_d$) and dimerization ($K_{dim}$) equilibria are evident in an isothermal microcalorimetry study as well. The helical content increases to a maximum value of 25%, both with excess Eu(III) and with the stabilization afforded by TFE solvent. This behavior is consistent with EuP3 adopting a defined rather than random structure in solution, in which metal-binding organizes the central loop region, and nucleates helix formation at either terminus. The calcium adduct, in contrast, reaches only 14% helicity in the metal-saturated form. This helicity difference may be due to a disparity in Ln(III)/Ca(II) dimerization behavior, as was observed for an abbreviated 13-mer EF-Hand loop peptide (Wójcik et al., 1997). The higher rigidity of the loop structure in the presence of the trivalent metals helps to explain why Ln(III) ions, but not Ca(II) ions, induce dimerization in the P3 peptide as well.

Part of the affinity of native EF-Hands for Ca(II) is due to the propensity of these motifs to occur in pairs within proteins (Falke et al., 1994). This tendency derives from the complementarity of the helix-loop-helix surfaces, and the hydrogen bonding of adjacent loops as short anti-parallel β-strands. Isolated EF-Hands peptides also dimerize in solution, forming back-to-back native-like folds (Maurer et al., 1995; Shaw et al., 1996; Monera et al., 1992). A metallated loop becomes a structural template for the folding of a second, apo-peptide into a back-to-back pair (MP•P). The metal ion does not bridge two EF-Hand motifs, but the dimerization is instead due to hydrophobic and β-sheet interfaces between strands. Thus, one equivalent of metal ion (M) organizes two equivalents of peptide (P). The second, lower affinity site (about 1 mM) is not populated until higher metal concentrations are reached, giving the full dimer (MP•PM) (Shaw et al., 1991). For native EF-Hand sequences, a monomeric intermediate (MP) is not even observed, as they instead fold directly to a MP•P form (Shaw et al., 1991; Shaw et al., 1990). As a result of the tertiary interactions, dimerization of the EF-Hand motif is favored even with truncated loops (Wójcik et al., 1997).

In addition to the CD titration results, further evidence for dimer formation and insight into the structure of the metallopeptides comes from NMR. The conformational changes in P3 with metal binding were followed by $^1$H-NMR spectroscopy. The appearance and increase of new peaks upon the addition of Eu(III) (*, • in FIG. 5) are consistent with slow-exchange kinetics of metal-binding and dimerization. However, there are no well-defined peaks outside the diamagnetic window to indicate a close and rigidly constrained proximity to the paramagnetic ion. This observation is consistent with greater flexibility of the metal-binding region in the synthetic peptide, relative to native EF-Hands. This local flexibility would further exchange-broaden peaks arising from residues in close proximity to the paramagnetic metal and render them unobservable under these conditions.

Most changes in the P3 spectrum occur within the first 0.5 equivalent of added Eu(III) (* in FIG. 5), supporting the conclusion that these peptides dimerize to the same singly-occupied structure $(Eu(P3)_2=MP•P)$ as native EF-Hand peptides. One metal ion structurally organizes two peptides. The few additional changes which occur between 0.5 and 1 equivalent Eu(III) (• in FIG. 5), reflect binding of a second metal, to give the fully occupied dimer $(Eu_2(P3)_2=MP•PM)$. This conclusion is supported by dilution studies (FIG. 6), in which lowering the EuP3 concentration from 0.96 mM to 0.33 mM results in a spectrum qualitatively similar to that of 0.5:1 Eu:P3, including the disappearance of peaks marked with • in FIG. 5. Over this dilution range, the first metal site remains fully occupied ($K_d \leq 20$ μM), and the monomeric EuP3 is less favored than a singly occupied dimer form ($K_{dim}$=80 μM). However, at the highest concentrations (approaching 1 mM Eu:P3), the lower affinity metal site must also become populated ($K_{d2}$ about 1 mM), and this is reflected in the NMR spectral changes.

The synthetic peptide mimics its EF-Hand parent in its affinity for Eu(III) and Ca(II), and its tendency to dimerize. The legacy of the synthetic peptide's other parent motif is the DNA-binding affinity of the homeodomains. Agarose gel shift assays of EuP3 shows that the metallopeptide exhibits DNA-binding affinity in the micromolar regime. The DNA-binding is predominantly due to electrostatic interactions, as evidenced by the affinity of free P3. At pH=7, P3 has 10 positively charged residues, and three of the seven acidic residues (Asp, Glu) are charge-balanced by Eu(III) binding. Though P2 has two fewer basic residues, metallated P2 should still have greater total positive charge than apo-P3 (at pH=7, +4 versus +3, respectively). Thus, by electrostatic attraction alone, EuP2 should have greater affinity for DNA than free P3. However, neither P2 nor EuP2 has appreciable DNA affinity over the concentration range studied (5–25 μM). This suggests that the inherent tendency to fold evidenced by EuP3 (but not EuP2) plays some role in interactions with B-form DNA. This is expected if the synthetic peptide associates with the DNA major groove, as do native HTH domains.

Thus, a chimeric peptide motif can be prepared from two unrelated but topologically equivalent parent structures, while retaining the functions and features of the parent domains. The exemplified synthetic peptide binds Ca(II) and Eu(III) in a manner analogous to native EF-Hands, has solution structure and behavior consistent with a defined, helical fold, and exhibits significant affinity for supercoiled DNA as do HTH-containing repressors.

REFERENCES

Abdallah et al., *Biol. Cell*, 85, 1 (1995).
Akke et al., *J. Mol. Biol.*, 200, 173 (1991).
Almquist et al., *J. Med. Chem.*, 23, 1392 (1980).
Bashkin et al., *J. Am. Chem. Soc.*, 116, 5981 (1994).
Basile et al., *J. Am. Chem. Soc.*, 109, 7550 (1987).
Bavaay and Merrifield, The Peptides (E. Gross and F. Meienhofer eds., Academic Press, 1980).
Bird et al., *Science*, 242, 424 (1988).
Bradford, *Anal. Biochem.*, 72, 248 (1976).
Brennan et al., *Trends Biochem. Sci.*, 14, 286 (1989).
Bruno et al., *Biochemistry*, 31, 7016 (1992).
Burley et al., *Curr. Opin. in Struct. Biol.*, 4, 3 (1994).
Burroughs et al., *Biochemistry*, 33, 10428 (1994).
Cammers-Goodwin et al., *J. Am. Chem. Soc.*, 118, 3092 (1996).
Celio et al., Guidebook to the Calcium Binding Proteins (Sambrook and Tooze Publication at Oxford Univ. Press 1996).
Chappel et al., *Inorg Chem.*, 37, 3989–3998 (1998).
Chattopadhyaya et al., *J. Mol. Biol.*, 228, 1177 (1992).
Chen et al., *Biochemistry*, 11, 4120 (1972).
Chen et al., *J. Biol. Chem.*, 273, 13537 (1998).
Chin et al., *J. Am. Chem. Soc.*, 111, 186 (1989).

Clark et al., *Analy. Biochem.*, 213, 296 (1993).
Clarke et al., *Protein Sci.*, 3, 1779 (1994).
Clark-Lewis et al., *Meth. Enzymol.*, 287, 233 (1997).
Coruh et al., *Biochemistry*, 31, 7970 (1994).
Dadlez et al., *FEBS Lett.*, 282, 143 (1991).
Dayhoff, Atlas of Protein Sequence and Structure, volume 5, National Biomedical Research Foundation, pp. 101–110, and Supplement 2 to this volume, pp. 1–10 (1972).
DeGrado et al., *Annu. Rev. Biochem.*, 68, 779–819 (1999).
Derossi et al., *Trends Cell Biol.*, 8, 84 (1998).
Dixon et al., *J. Chem. Soc. Chem. Commun.*, 1287 (1996).
Donnelly et al., *Ann. N.Y. Acad. Sci.*, 772, 40 (1995).
Drake et al., *Biochemistry*, 35, 6697 (1996).
Efimov, *FEBS Lett.*, 166, 33 (1984).
Efimov, *FEBS Lett.*, 355, 213 (1994).
Efimov, *FEBS Lett.*, 391, 167 (1996).
Efimov, *Proteins: Structure, Function and Genetics*, 28, 241 (1997).
Evans et al., *J. Med. Chem.*, 30, 1229 (1987).
Fahraeus et al., *J. Pathol.*, 187, 138–146 (1999).
Falke et al., *Quart. Rev. Biophys.*, 27, 219 (1994).
Falke et al., *Biochemistry*, 30, 8690 (1991).
Fauchere, *Adv. Drug Res.*, 15, 29 (1986).
Fraenkel et al., *Nat, Struct. Biol.*, 5, 692 (1998).
Freemont et al., *Biochem. J.*, 1 (1991).
Gehring et al., *Annu. Rev. Biochem.*, 63, 487 (1994).
Gibney, et al., *Curr. Opin. Chem. Biol.*, 1, 537–542 (1997).
Gillies et al., *Biotechnol.*, 7, 798–804 (1989).
Gillies et al., *J. Immunol. Meth.*, 125, 191 (1989).
Gius et al., *Cancer Res.*, 59, 2577 (1999).
Glover & Harrison, *Nature*, 373, 257 (1995).
Goch, *Acta. Biochem. Pol.*, 46, 673 (1999).
Guex et al., *Electrophoresis*, 18, 2714 (1997).
Hann, M. M., *J. Chem. Soc. Perkin Trans.*, I, 307 (1982).
Hashimoto et al., *J. Chem. Soc. Perkin. Trans.*, I, 2623 (1996).
Hayashi et al., *Inorg. Chem.*, 32, 5899 (1993).
Hegg et al., *Inorg. Chem.*, 35, 7474 (1996).
Hellinga, *Folding Des.*, 3, R1–R8 (1998).
Hettich et al., *J. Chem. Soc. Perkin. Trans.*, II, 2069 (1997a).
Hettich et al., *J. Am. Chem. Soc.*, 119, 5638 (1997b).
Holladay et al., *Tetrahedron Lett.*, 24, 4401 (1983).
Hruby, *Life Sci.*, 31, 189 (1982).
Huang et al., *J. Protein Chem.*, 15, 481 (1996).
Hudson et al., *Int. J. Pept. Prot. Res.*, 14, 177 (1979).
Huston et al., *Proc. Nat. Acad. Sci.*, 85, 5879 (1988).
Itoh et al., *J. Chem. Soc. Chem. Commun.*, 677 (1997).
Jennings-White et al., *Tetrahedron Lett.*, 23, 2533 (1982).
Jones et al., *Nature*, 321, 522 (1986).
Kanaya et al., *J. Biol. Chem.*, 267, 8492 (1992).
Kim et al., *Proc. Natl. Acad. Sci.*, 91, (1994).
Kim et al., *Proc. Natl. Acad. Sci.*, 93, 1156 (1996).
Kim et al., *Biol. Chem.*, 379, 489 (1998).
Kissinger et al., *Cell*, 63, 579 (1990).
Kissinger et al., *Nature*, 378, 641 (1995).
Kissinger et al., *Cell*, 63, 579 (1990).
Klemm et al., *Cell*, 77, 21 (1994).
Komiyama et al., *Chem. Express*, 8, 85 (1993a).
Komiyama et al., *Chem. Lett.*, 1025 (1994a).
Komiyama et al., *Supramol. Chem.*, 4, 31 (1994b).
Komiyama et al., *Nucleosides Nucleotides*, 13, 1297 (1994c).
Kornberg, *J. Biol. Chem.*, 268, 26813 (1993).
Laughon, *Biochemistry*, 30, 11357 (1991).
Lehrman et al., *Biochemistry*, 29, 5590 (1990).
Li et al., *Proc. Natl. Acad. Sci.*, 90, 2764 (1992).
Li et al., *Proc. Natl. Acad. Sci.*, 89, 4275 (1993).
Lindgren et al., *Trends Pharma. Sci.*, 21, 99 (2000).
Lombardi et al., *Proc Nat Acad Sci USA*, 97, 6298–6305 (2000).
Luo et al., *Biochemistry*, 36, 8413 (1997).
Magda et al., *J. Am. Chem. Soc.*, 116, 7439 (1994).
Matsumura et al., *J. Chem. Soc. Chem. Commun.*, 2019 (1994).
Maurer et al., *J. Mol. Biol.*, 257, 347 (1995).
Meienhofer, Hormonal Proteins and Peptides (C.H. Li ed. Academic Press, 1973).
Merrifield, *J. Am. Chem. Soc.*, 85, 2149 (1963).
Molling, *J. Mol. Med.*, 75, 242 (1997).
Monera et al., *Protein Sci.*, 1, 945 (1992).
Morgan and Foon, Monoclonal Antibody Therapy to Cancer: Preclinical Models and Investigations, *Basic and Clinical Tumor Immunology*, (Kluwer Academic Publishers, Hingham, Mass.).
Morley, *Trends. Pharm. Sci.*, 463 (1980).
Morrison et al., *Proc. Nat. Acad. Sci.*, 81, 6851 (1984).
Morrow et al., *Models in Inorganic Chemistry*, 9, 41 (1994).
Needleman and Wunsch, *J. Mol. Biol.*, 48, 443 (1970).
Ott et al., *Appl. Microbiol. Biotechnol.*, 52, 761–767 (1999).
Pabo et al., *Annu. Rev. Biochem.*, 53, 293 (1984).
Pardoll et al., *Immunity*, 3, 165 (1995).
Patikoglou et al., *Annu. Rev. Biophys. Biomol. Struct.*, 26, 289 (1997).
Fundamental Immunology (Paul, W. E. ed., Raven Press 1984).
Pearson and Lipman, *Proc. Natl. Acad. Sci.*, 85, 2444 (1988).
Pomerantz et al., *Science*, 267, 93 (1995).
Prochiantz, *Ann. NY Acad. Sci.*, 886, 172 (1999).
Rammo et al., *J. Chem. Soc. Chem. Commun.*, 105 (1996).
Rammo et al., *Liebigs Ann.*, 1757 (1996a).
Rammo et al., *Inorg Chim. Acta.*, 251, 125 (1996b).
Regan, *Curr. Opin. Struct. Biol.*, 9, 494–499 (1999).
Reynolds et al., *Nucleic Acids Res.*, 24, 760 (1996).
Richardson et al., *Biophys. J.*, 63, 1186 (1992).
Roquet et al., *J. Mol. Biol.*, 223, 705 (1992).
Roth et al., *J. Nat. Cancer Inst.*, 89, 21–39 (1997).
Sagripanti et al., *J. Biol. Chem.*, 264, 1729 (1989).
Sambrook et al., "Expression of cloned genes in *Escherichia coli*." In Molecular Cloning: A Laboratory Manual (1989).
Saxena et al., *Proc. Nat. Acad. Sci.*, 68, 969 (1971).
Schnaith et al., *Proc. Natl. Acad. Sci.*, 91, 569 (1994).
Schwabe et al., *Cell*, 75, 567 (1993).
Schwage et al., *Nature Struct. Biol.*, 1, 345 (1994).
Schwarze et al., *Trends Cell Biol.*, 10, 290 (2000).
Schwarze et al., *Science*, 285, 1569 (1999).
Shaw et al., *J. Am. Chem. Soc.*, 113, 5557 (1991).
Shaw et al., *Science*, 249, 280 (1990).
Shaw et al., *Biochemistry*, 35, 7429 (1996).
Siedlecka et al., *Proc. Natl. Acad. Sci.*, 96, 903 (1999).
Simmons et al., *Science*, 276, 276 (1997).
Smith and Waterman *Adv. Appl. Math.*, 2, 482 (1981).
Spatola, *Vega Data*, 1, "Peptide Backbone Modifications" (1983).
Spatola, Chemistry and Biochemistry of Amino Acids, Peptides, and Proteins (B. Weinstein, ed. Marcel Dekker 1983).
Spatola et al., *Life Sci.*, 38, 1243 (1986).
Starrs et al., *Biopolymers*, 32, 1695 (1992).
Stewart et al., Solid Phase Peptide Synthesis (W. H. Freeman Co. 1969).
Tagasaki et al., *J. Am. Chem. Soc.*, 116, (1994).
Tanaka et al., *J. Mol. Recognit.*, 3, 156 (1990).

Treisman et al., *BioEssays*, 14, 145 (1992).
Truwick et al., *Chem. Rev.*, 98, 939–960 (1998).
Tucker-Kellogg et al., *Structure (London)*, 5, 1047 (1997).
Uchiyama et al., *Bioconjugate Chem.*, 5, 327 (1994).
Uhr, *J. of Immunol.* 133, i–vii (1984).
Veber et al., *T.I.N.S.*, 392 (1985).
Vlassov et al., *Antisense Nucleic Acid Drug Dev.*, 7, 39 (1997).
Wójcik et al., *Biochemistry*, 36, 680 (1997).
Wolberger et al., *Cell*, 67, 517 (1991).
Yang et al., *Mol. Med. Today*, 2, 476 (1996).
Zhu et al., *J. Mol. Catal.*, 135, 107(1998).
Zucherman et al., *J. Am. Chem. Soc.*, 110, 6594 (1988).
Zucherman et al., *Proc. Natl. Acad. Sci.*, 86, 1766 (1989).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

---

What is claimed is:

1. An isolated synthetic peptide or polypeptide comprising a domain which specifically binds a nucleic acid sequence linked to a domain which specifically binds a metal which is hydrolytically or redox active linked to a further domain which specifically binds a nucleic acid sequence, wherein the domain which binds a metal is capable of binding a lanthanide, calcium or a metal in the same group as calcium.

2. The peptide or polypeptide of claim 1 which comprises the amino acid sequence TERRRQQLDKDGDGTIDEREIKIHFQNKRAKIK (SEQ ID NO:2), or a portion thereof which binds the nucleic acid sequence and the metal.

3. The peptide or polypeptide of claim 1 which comprises the amino acid sequence TERRRFDKDGNGYISAAELRHVKIWFQNKRAKIK (SEQ ID NO:3), or a catalytically active portion thereof.

4. The peptide or polypeptide of claim 1 which comprises TERRRFRVFDKDGNGYISAAEKIWFQNKRAKIK (SEQ ID NO:4), or a catalytically active portion thereof.

5. The peptide or polypeptide of claim 1 which comprises the amino acid sequence TRRRRFLSFDKDGDGTITTKEEVWFQNRRMKWK (SEQ ID NO:5), or a catalytically active portion thereof.

6. The peptide or polypeptide of claim 1 which comprises the amino acid sequence DEKRPRTAFSGEQLARLKREFNENRYLTERRRLRVFDKDGNGF ISAAEKI WFQNK RAKIKKST (SEQ ID NO:6), or a catalytically active portion thereof.

7. The peptide or polypeptide of claim 1 which comprises the amino acid sequence TERRRQQLDKDGDGTIDEREIKIWFQNKRAKIK (SEQ ID NO:7), or a catalytically active portion thereof.

8. The peptide or polypeptide of claim 1 which comprises the amino acid sequence FRVFDKDGNGYISAAEKIWF (SEQ ID NO:8), or a catalytically active portion thereof.

9. The peptide or polypeptide of claim 1 which comprises at least 20 residues.

10. The peptide or polypeptide of claim 1 which comprises a consensus EF-Hand sequence.

11. The peptide or polypeptide of claim 1 wherein one domain which specifically binds a nucleic acid sequence is a domain from a transcription factor.

12. The peptide or polypeptide of claim 1 wherein one domain which specifically binds a nucleic acid sequence comprises a helix or a strand from a helix-turn-helix motif, a relaxed helix-turn-helix motif, a winged helix-turn-helix motif, a helix-loop-strand motif, or a hormone receptor motif.

13. The peptide or polypeptide of claim 1 which binds dsDNA, dsRNA, ssDNA, ssRNA, A-DNA, B-DNA, or Z-DNA.

14. The peptide or polypeptide of claim 11 wherein the transcription factor is engrailed.

15. The peptide or polypeptide of claim 1 wherein the domains which specifically bind nucleic acid are from a homeodomain.

16. The peptide or polypeptide of claim 11 wherein the transcription factor comprises a helix-turn-helix domain.

17. The peptide or polypeptide of claim 12 which comprises alpha-helices 2 and 3 of a helix-turn-helix motif.

18. The peptide or polypeptide of claim 1 which binds Ca(II) or Mg(II).

19. The peptide or polypeptide of claim 1 which binds Eu(III).

20. The peptide or polypeptide of claim 1 further comprising a protein transport domain.

21. The peptide or polypeptide of claim 1 which binds a lanthanide (III) or (IV).

22. The peptide or polypeptide of claim 1 wherein the lanthanide is cerium, praseodymium, neodymium, promethium, samanum, europium, gadolinium, terbium, dysprosium, holmium, erbium, thulium, ytterbium, or lutetium.

23. An isolated nucleic acid molecule comprising a nucleic acid segment which encodes the peptide or polypeptide of claim 1, or a sequence complementary thereto.

24. An expression cassette comprising the nucleic acid molecule of claim 23 which is operably linked to a promoter functional in a host cell.

25. A host cell comprising the expression cassette of claim 24.

26. The host cell of claim 25 wherein the host cell is a prokaryotic cell.

27. The host cell of claim 25 wherein the host cell is a eukaryotic cell.

28. The host cell of claim 25 wherein the host cell is a plant cell.

29. A vector comprising the expression of cassette of claim 24.

30. A method of using a synthetic endonuclease specific for a particular nucleic acid sequence comprising: contacting a sample comprising isolated nucleic acid with an amount of the peptide or polypeptide of claim 1 effective to cleave at least one nucleic acid sequence in the sample.

31. A method to detect the presence of a nucleic acid sequence in a sample comprising:
  a) contacting a sample comprising nucleic acid suspected of containing a nucleic acid sequence recognized by the peptide or polypeptide of claim 1, with the peptide or polypeptide of claim 1; and
  b) determining or detecting whether the peptide or polypeptide cleaves the nucleic acid sequence.

32. The method of claim 31 wherein the detection or determination is by gel electrophoresis.

* * * * *

UNITED STATES PATENT AND TRADEMARK OFFICE
CERTIFICATE OF CORRECTION

| | |
|---|---|
| PATENT NO. | : 7,091,026 B2 |
| APPLICATION NO. | : 09/785546 |
| DATED | : August 15, 2006 |
| INVENTOR(S) | : Franklin |

It is certified that error appears in the above-identified patent and that said Letters Patent is hereby corrected as shown below:

On the face page, in field (56), under "Other Publications", in column 1, line 9, delete "Hyrdolysis" and insert -- Hydrolysis --, therefor.

On page 2, in field (56), under "Other Publications", in column 1, line 21, delete "phophate" and insert -- phosphate --, therefor.

On page 2, in field (56), under "Other Publications", in column 2, line 2, delete "Honeodomain" and insert -- Homeodomain --, therefor.

On page 2, in field (56), under "Other Publications", in column 2, line 32, delete "calcium-bing" and insert -- calcium-binding --, therefor.

In column 3, line 1, delete "rubridoxin," and insert -- rubredoxin, --, therefor.

In column 5, line 54, delete "righe; parvalbumiun" and insert -- right; parvalbumin --, therefor.

In column 6, line 2, delete "shown" and insert -- shown; --, therefor.

In column 6, line 2, delete "sitein;" and insert -- site; in --, therefor.

In column 6, line 61, delete "EuCl3" and insert -- $EuCl_3$ --, therefor.

In column 6, line 66, delete "intesity," and insert -- intensity, --, therefor.

In column 15, line 21, delete "statine," and insert -- statin, --, therefor.

In column 15, line 22, delete "citruline," and insert -- citrulline, --, therefor.

UNITED STATES PATENT AND TRADEMARK OFFICE
CERTIFICATE OF CORRECTION

| | | |
|---|---|---|
| PATENT NO. | : 7,091,026 B2 | |
| APPLICATION NO. | : 10/785546 | |
| DATED | : August 15, 2006 | |
| INVENTOR(S) | : Franklin | |

It is certified that error appears in the above-identified patent and that said Letters Patent is hereby corrected as shown below:

In column 17, line 30, delete "fall" and insert -- full --, therefor.

In column 18, line 52, delete "i.e," and insert -- i.e., --, therefor.

In column 24, line 56, after "hydrogel" delete "gel".

In column 24, line 58, delete "ethylenvinyl" and insert -- ethyl vinyl --, therefor.

In column 27, line 4, delete "Komberg," and insert -- Kornberg, --, therefor.

In column 28, line 27, delete "(LTCO)" and insert -- (ITCO) --, therefor.

In column 29, line 26, delete "pH7.5." and insert -- pH=7.5. --, therefor.

In column 33, line 66, delete "$6 \times 10^{-1}$)" and insert -- $6 \times 10^{-11}$) --, therefor.

In column 34, line 17, delete "supernatent" and insert -- supernatant --, therefor.

In column 34, line 22, delete "has" and insert -- had --, therefor.

In column 36, line 46, delete "200," and insert -- 220, --, therefor.

In column 38, line 8, delete "257," and insert -- 253, --, therefor.

In column 43, line 30, in Claim 4, after "comprises" insert -- the amino acid sequence --.

UNITED STATES PATENT AND TRADEMARK OFFICE
CERTIFICATE OF CORRECTION

PATENT NO. : 7,091,026 B2
APPLICATION NO. : 10/785546
DATED : August 15, 2006
INVENTOR(S) : Franklin It is certified that error appears in the above-identified patent and that said Letters Patent is hereby corrected as shown below:

In column 43, lines 38-40, in Claim 6, delete "DEKRPRTAFSGEQLARLKREFNENRYLTERRRLRVFDKDGNGF ISAAEKI WFQNK RAKIKKST" and insert -- DEKRPRTAFSGEQLARLKREFNENRYLTERRRLRVFD KDGNGFISAAEKIWFQNKRAKIKKST --, therefor.

In column 44, line 30, in Claim 22, delete "samanum," and insert -- samarium, --, therefor.

Signed and Sealed this

Eighth Day of July, 2008

JON W. DUDAS
*Director of the United States Patent and Trademark Office*

SEQUENCE LISTING

```
<160> NUMBER OF SEQ ID NOS: 8

<210> SEQ ID NO 1
<211> LENGTH: 33
<212> TYPE: PRT
<213> ORGANISM: Artificial Sequence
<220> FEATURE:
<223> OTHER INFORMATION: A synthetic peptide.

<400> SEQUENCE: 1

Glu Arg Arg Arg Gln Gln Leu Ser Ser Glu Ala Glu Thr Ile Phe Gly
1               5                   10                  15

Asp Gly Asp Lys Asp Glu Ile Lys Ile Trp Phe Gln Asn Lys Arg Ala
            20                  25                  30

Lys

<210> SEQ ID NO 2
<211> LENGTH: 33
<212> TYPE: PRT
<213> ORGANISM: Artificial Sequence
<220> FEATURE:
<223> OTHER INFORMATION: A synthetic peptide.

<400> SEQUENCE: 2

Thr Glu Arg Arg Arg Gln Gln Leu Asp Lys Asp Gly Asp Gly Thr Ile
1               5                   10                  15

Asp Glu Arg Glu Ile Lys Ile His Phe Gln Asn Lys Arg Ala Lys Ile
            20                  25                  30

Lys

<210> SEQ ID NO 3
<211> LENGTH: 34
<212> TYPE: PRT
<213> ORGANISM: Artificial Sequence
<220> FEATURE:
<223> OTHER INFORMATION: A synthetic peptide.

<400> SEQUENCE: 3

Thr Glu Arg Arg Arg Phe Asp Lys Asp Gly Asn Gly Tyr Ile Ser Ala
1               5                   10                  15

Ala Glu Leu Arg His Val Lys Ile Trp Phe Gln Asn Lys Arg Ala Lys
            20                  25                  30

Ile Lys

<210> SEQ ID NO 4
<211> LENGTH: 33
<212> TYPE: PRT
<213> ORGANISM: Artificial Sequence
```

```
<220> FEATURE:
<223> OTHER INFORMATION: A synthetic peptide.

<400> SEQUENCE: 4

Thr Glu Arg Arg Arg Phe Arg Val Phe Asp Lys Asp Gly Asn Gly Tyr
1               5                   10                  15

Ile Ser Ala Ala Glu Lys Ile Trp Phe Gln Asn Lys Arg Ala Lys Ile
            20                  25                  30

Lys

<210> SEQ ID NO 5
<211> LENGTH: 33
<212> TYPE: PRT
<213> ORGANISM: Artificial Sequence
<220> FEATURE:
<223> OTHER INFORMATION: A synthetic peptide.

<400> SEQUENCE: 5

Thr Arg Arg Arg Arg Phe Leu Ser Phe Asp Lys Asp Gly Asp Gly Thr
1               5                   10                  15

Ile Thr Thr Lys Glu Glu Val Trp Phe Gln Asn Arg Arg Met Lys Trp
            20                  25                  30

Lys

<210> SEQ ID NO 6
<211> LENGTH: 63
<212> TYPE: PRT
<213> ORGANISM: Artificial Sequence
<220> FEATURE:
<223> OTHER INFORMATION: A synthetic peptide.

<400> SEQUENCE: 6

Asp Glu Lys Arg Pro Arg Thr Ala Phe Ser Gly Glu Gln Leu Ala Arg
1               5                   10                  15

Leu Lys Arg Glu Phe Asn Glu Asn Arg Tyr Leu Thr Glu Arg Arg Arg
            20                  25                  30

Leu Arg Val Phe Asp Lys Asp Gly Asn Gly Phe Ile Ser Ala Ala Glu
        35                  40                  45

Lys Ile Trp Phe Gln Asn Lys Arg Ala Lys Ile Lys Lys Ser Thr
    50                  55                  60

<210> SEQ ID NO 7
<211> LENGTH: 33
<212> TYPE: PRT
<213> ORGANISM: Artificial Sequence
<220> FEATURE:
<223> OTHER INFORMATION: A synthetic peptide.

<400> SEQUENCE: 7

Thr Glu Arg Arg Arg Gln Gln Leu Asp Lys Asp Gly Asp Gly Thr Ile
1               5                   10                  15

Asp Glu Arg Glu Ile Lys Ile Trp Phe Gln Asn Lys Arg Ala Lys Ile
            20                  25                  30

Lys

<210> SEQ ID NO 8
<211> LENGTH: 20
<212> TYPE: PRT
<213> ORGANISM: Artificial Sequence
<220> FEATURE:
<223> OTHER INFORMATION: A synthetic peptide.
```

```
-continued

<400> SEQUENCE: 8

Phe Arg Val Phe Asp Lys Asp Gly Asn Gly Tyr Ile Ser Ala Ala Glu
 1               5                  10                  15

Lys Ile Trp Phe
            20
```